United States Patent [19]
Nashimoto et al.

[11] Patent Number: 5,747,053
[45] Date of Patent: May 5, 1998

[54] ANTIVIRAL FILTER AIR CLEANER IMPREGNATED WITH TEA EXTRACT

[75] Inventors: Kazuo Nashimoto; Yoshikazu Tashiro; Yoshiomi Kosaka, all of Chigasaki; Yukihiko Hara, Fujieda, all of Japan

[73] Assignees: Matsushita Seiko Co., Ltd., Osaka; Mitsui Norin Co., Ltd., Tokyo, both of Japan

[21] Appl. No.: 647,012

[22] Filed: May 9, 1996

[30] Foreign Application Priority Data

May 11, 1995 [JP] Japan ................... 7-112850
Jun. 8, 1995 [JP] Japan ................... 7-141513

[51] Int. Cl.$^6$ ........................................ A47J 31/00
[52] U.S. Cl. ........................... 424/405; 55/350.1
[58] Field of Search ........................... 210/507, 508, 210/504; 422/123; 424/404, 222, 76.9; 206/439; 58/350.1, 95, 285

[56] References Cited

U.S. PATENT DOCUMENTS

5,240,487  8/1993  Kung ........................... 55/486

FOREIGN PATENT DOCUMENTS

| 59-219384 | 12/1984 | Japan . |
| 6013780 | 1/1985 | Japan . |
| 61-130285 | 6/1986 | Japan . |
| 3-101623A | 4/1991 | Japan . |
| 3101623 | 4/1991 | Japan . |

OTHER PUBLICATIONS

Japio Abstract No. 04–319356 & JP040319356 A; Nov. 10, 1992; (Katerun).
Japio Abstract No. 04–077424 & JP040077424 A; Mar. 11, 1992; (Lotte).
Japio Abstract No. 02–189153 & JP020189153 A; Jul. 25, 1990; (Kobayashi).
Japio Abstract No. 62–169719 & JP620169719 A; Jul. 25, 1987; (Sunstar).
WPI Abstract Acc No. 95–379965/49 & JP070258054 A; Oct. 9, 1995; (Itoen).
WPI Abstract Acc No. 91–285174/39 & JP030188848 A; Aug. 16, 1991; (Hitata).
WPI Abstract Acc No. 89–260889/36 & JP010190624 A; Jul. 31, 1989; (Itoen).
WPI Abstract Acc No. 89–147372/20 & JP010090124 A; Apr. 6, 1989; (Taiyo).

*Primary Examiner*—Thurman K. Page
*Assistant Examiner*—D. Faulkner
*Attorney, Agent, or Firm*—Watson Cole Stevens Davis, P.L.L.C.

[57] ABSTRACT

The present invention provides a medicated gargling cup with which it is possible to form a liquid for gargling effective for preventing cold by merely pouring water into the cup; an antiviral mask having a nonwoven fabric impregnated with a tea extract, which mask can be easily produced commercially and is capable of maintaining a high virus trapping performance, inactivating the trapped viruses and preventing them from being rescattered; an antiviral filter and an antifungal, antibacterial and antiviral filter comprising in laminations a dust collecting filter and a filter impregnated with a tea extract; an air cleaner and an air cleaner-humidifier comprising the antiviral filter.

25 Claims, 14 Drawing Sheets

ANTIVIRAL FILTER AIR CLEANER IMPREGNATED WITH TEA EXTRACT

BACKGROUND OF THE INVENTION

The present invention relates to the antiviral techniques making use of tea extracts having the effect of inactivating the viruses. More particularly it relates to a cup used for gargling for preventing cold caused by the influenza viruses, etc.; an antiviral mask which can prevent the infectious viruses from entering the mask wearer's system from the mouth and/or the nose by trapping the viruses floating in the air at a high rate and inactivating the trapped viruses; an antiviral filter which is capable of trapping the viruses floating in the ambient air at a high rate and inactivating the trapped viruses to clean the air; an antifungal, antibacterial and antiviral filter which can trap fungi, bacteria and/or viruses floating in the air to kill or inactivate the trapped fungi, bacteria and/or viruses, thereby to clean the air; an air cleaner; and an air cleaner-humidifier comprising said filter.

DESCRIPTIONS OF RELATED PRIOR ART

Liquid gargling agents have been hitherto commercially available, and in use thereof, they were usually put into a cup containing water to form a liquid for gargling. Various types of gargling agents have been placed on the market, among which tea polyphenols, which are the natural tea extracts having a potency to inactivate the influenza viruses, are known as a typical example (Patent Kokai No. 3-101623).

The influenza viruses, which are pathogenic viruses of cold, tend to cause spread of influenza through aerial or droplet infection at a crowded place, so the development of an antiviral mask capable of trapping and inactivating the influenza viruses to prevent the infectious viruses from entering a human body has been desired.

Ultraviolet irradiation has been known as a means for inactivating the viruses.

The size of the viruses is as small as about 0.1 µm, and it is considered that the viruses float in the air while integrated into or combined with the moisture or dust particles. The conventional mask, as shown in FIG. 23, consisted of a nonwoven fabric 102 and a pair of strings 103 to be passed round the ears, and if a HEPA filter, a high- or medium-performance filter or an electret filter was applied as the nonwoven fabric 102 as in the shown mask 101, it was possible to trap the viruses by the mask.

Development of an antiviral filter capable of eliminating or inactivating the influenza viruses to clean the ambient air and an air cleaner or air cleaner-humidifier comprising such a filter has also been desired.

No technique is available on utilization of an inactivating agent in this type of devices. It is, however, possible to trap the viruses with the known types of filter, such as HEPA filter, high- or medium-performance filter and electret filter.

In the field of such a filter, it generally has been carried out to kill a microorganism such as fungi and bacteria, but a human disease caused by a microorganism is mainly based on viruses. Accordingly, it has been desired that the air in facilities such as a hospital, a school and an old age home to which many people having poor resistances gather is cleaned to inactivate viruses.

As shown in FIG. 24, a dust-collecting unit 104 is provided with nonwoven fabric filter medium in a pleat state or a plate state. A nonwoven fabric such as a glass fiber and polypropylene is used for the nonwoven fabric filter medium 105 and an antifungal/antibacterial agent may be often applied on the surface of the filter medium 105. Air is blown in the dust-collecting unit 104 using an air conditioner or air blower and dusts suspended in the air or in a room may be trapped with the nonwoven fabric filter medium 105.

Fungi, bacterial and/or viruses are also contained in the trapped dusts and such microorganisms are accumulated within the nonwoven fabric filter medium 105, thereby there is the possibility that the microorganisms are propagated therein.

When an antifugal agent or antibacterial agent is applied to the nonwoven fabric 105, fungi and/or bacteria may be killed.

The antifungal agent used in the nonwoven fabric includes organic nitrogen compound, organic sulfur compound, organic acid ester, organic iodine compound, imidazole compound or benzol compound, and the antibacterial agent includes silver compound, zinc compound, alcohol compound, phenol compound, quaternary ammonium salt, benzoic acids, hydrogen peroxide, cresol, chlorhexidin, nitrogen-series antifungal agent, aldehydes, sorbic acid or the like.

The gargling agent and the cup are usually kept separate from each other in such a conventional gargling agent, so that when one wants to gargle, it is required to first put water into the cup and then put an appropriate amount of gargling agent therein. When influenza is prevalent, it is highly probable that a person be infected with influenza if he goes to a crowded place or a hospital, so that it is more effective for prevention of influenza to gargle soon after leaving the crowded place or the hospital or at the spot than gargling after returning home. Therefore, for making effective gargling, it is required for you to always carry with you both a gargling agent and a cup since each of them is indispensable for effective gargling. It is also essential to dispense an optimal amount of gargling agent for each gargling since the use of a greater amount of gargling agent than prescribed may prove detrimental to the health.

SUMMARY OF THE INVENTION

The present invention is intended to solve the prior art problems as mentioned above, and for this purpose it provides a medicated gargling cup characterized in that a proper amount of a gargling agent is attached to the cup so that you can prepare a liquid for effective gargling by merely pouring water into the cup.

The present invention also provides a medicated gargling cup characterized by use of a tea polyphenol having a high potent to inactivate the pathogenic viruses of cold such as influenza viruses as the gargling agent. This gargling agent is high in safety because of its natural extract, and can form a gargling liquid effective for preventing cold on pouring water into the cup.

The present invention is further intended to provide a medicated gargling cup capable of providing a gargling liquid with a greater effect of preventing cold because of use of a separated and purified tea polyphenol as the gargling agent.

In the case of the conventional gargling agents, it has been necessary for you to carry both a cup and a gargling agent, so that the cup itself has been required to be small in size and weight and handy to carry.

In order to solve such conventional problems, the present invention provides a lightweight, handy-to-carry and disposable gargling cup using paper or other suitable material.

It is also envisaged in this invention to provide a gargling cup characterized in that a proper amount of a gargling agent is impregnated in the cup itself so that the cup can be used a number of times for effective gargling.

It is also an object of the present invention to provide a gargling cup having a gargling agent coated thereon so that a gargling liquid with an optimal concentration of gargling agent will be provided on pouring water into the cup.

A further object of the present invention is to provide a gargling cup having a gargling agent incorporated therein so that the cup can be used a number of times for effective gargling and is also prolonged in service life.

It is also an object of the present invention to provide a gargling cup having a gargling agent coated thereon, said gargling agent being applied in the form of a paste so that when water is poured into the cup, the gargling agent will be immediately dissolved in water to form a liquid for gargling, eliminating the time otherwise required for dissolution of the gargling agent in water.

It is another object of the present invention to provide a gargling cup having a foldable structure which allows you to carry a plural number of cups so that you can gargle a plural number of times even when you are away from home.

It is a further object of the present invention to provide a gargling cup which is so designed that even when two or more cups are placed one on another, there is no possibility that the gargling agent applied on the inside of one cup be transferred to the outside of another cup placed thereon.

Now, let us take a look at the conventional masks of the type under discussion. It is indeed possible with the conventional masks to trap the viruses, but since the trapped infectious viruses stay on the filter, they may be scattered around when the mask wearer coughs or sneezes, or they may even enter the mask wearer's system with breathing.

The conventional masks also had the problem that application of ultraviolet rays in these masks is hardly possible as they are harmful to a human body.

It is possible to trap the viruses by the nonwoven fabric 102 (FIG. 20) of the mask 101, but in case the live cells exist, they may proliferate on the nonwoven fabric 102 and be rescattered in the ambient air while maintaining infectivity.

Also, when the mask wearer coughs or sneezes, the infectious viruses trapped by the mask 101 may be scattered around.

The present invention aims at eliminating these problems, and it is an object of the invention to provide an antiviral mask which can be easily produced commercially and is capable of inactivating the viruses trapped by a nonwoven fabric to prevent the infectious viruses from entering the mask wearer's system.

It is also envisaged in the present invention to provide an antiviral mask having improved virus trapping ability and capable of preventing the trapped infectious viruses from being scattered.

It is also an object of the present invention to provide an antiviral mask whose surface is colored in white so that the time for change of the mask and its service life will be clearly indicated.

It is a further object of the present invention to provide an antiviral mask impregnated with a tea polyphenol, which is a separated and purified tea extract, whereby the trapped viruses are inactivated more positively.

Another object of the present invention is to provide an antiviral mask incorporated with a deodorant to eliminate the smell of the tea extract and foul breath of the mask wearer.

The conventional filters is now discussed. In the prior art, application of ultraviolet rays in the ordinary residential spaces was inhibitive since ultraviolet rays are harmful to a human body. It is possible to inactivate the viruses trapped by the filter by application of ultraviolet rays, but ultraviolet rays are liable to cause deterioration of filter material and other accessory elements.

Also, although trapping of the viruses by the filter is possible, if the live cells exist, they may proliferate on the filter and be rescattered while maintaining activity.

The present invention is schemed to solve the above problems, and it is an object of the invention to provide an antiviral filter which can be produced commercially, can maintain a high virus trapping performance and is capable of inactivating the viruses and preventing them from being rescattered.

Although a conventional dust-collecting unit is possible to kill fungi and/or bacteria, said unit have no function of inactivating viruses which can be caused by many diseases. Thus, it is being desired to provide a filter for inactivating viruses in addition to the killing of fungi and/or bacteria.

The present invention is aimed to solve such problems and to provide an antifungal, antibacterial and antiviral filter by which fungi, bacteria and/or viruses can be positively killed to form a clear air.

Moreover, the antibacterial material and the antiviral material are often harmful to a human body. Even when such materials are released from nonwoven fabric or the like, it is important to use a material which is not harmful to a human body.

The object of the present invention is to provide an antifungal, antibacterial and antiviral filter which is produced of a natural substance and is not harmful to a human body, thereby bacteria can be killed and viruses can be inactivated.

Many of the antibacterial material and the antiviral material have a property difficult to solubilize in water so that it is difficult to process them industrially. Hence, the material easy to process is demanded.

The further object of the present invention is to provide an antifungal, antibacterial and antiviral filter having a strengthened activity of killing bacteria and inactivating viruses which can be industrially easily used.

The antifungal material has often properties of a sparingly soluble in water and of highly reactivity. Thus, the processability thereof is poor and the material having good processability is demanded.

The another object of the present invention is to provide an antifungal, antibacterial and antiviral filter having a strengthened activity of killing fungi by using a highly dispersible antifungal agent, thereby it is easily used industrially.

The dimensions of fungi, bacteria and viruses are different and when said microorganisms are trapped in same nonwoven fabric, there was a possibility of lowering the effects of the respective materials.

The present invention is aimed to solve such a problem and to provide an antifungal, antibacterial and antiviral filter which can effectively trap fungi, bacteria and/or viruses in the nonwoven fabric and the growth of said microorganisms on the fabric may be prevented.

Generally, highly reactive chemical compounds such as antifungal agent, antibacterial agent and antiviral agent are coagulated and emulsion-precipitated and when they are applied in the nonwoven fabric, they are caused by discoloration of the nonwoven fabric and lowered processability, thereby the preparation of the filter was difficult.

The object of the present invention is to provide an antifungal, antibacterial and antiviral filter using the materials which can enhance the dispersability and processability, and shorten the time of producing the filter.

Moreover, when air conditioner etc is run for a long time, dusts are increasingly accumulated on the surface of the nonwoven fabric. The antifungal material, antibacterial material and antiviral material applied on the surface of the nonwoven fabric filter medium have a poor effect of killing or inactivating said microorganisms on the surface of the accumulated dusts and there was a possibility that said microorganisms accumulated on the surface of the filter may be grown.

The object of the present invention is to provide an antifungal, antibacterial and antiviral filter in which the antifungal agent, antibacterial agent and antiviral agent may be deliquenscenced in the dusts to kill and inactivate them positively.

When the antifungal material with the antibacterial and antiviral material is mixed followed by impregnation in nonwoven fabric, an excess amount of the antifungal material and the antibacterial/antiviral material are included therein, thereby the productivity thereof was lowered.

The present invention is aimed to provide an antifungal, antibacterial and antiviral filter which can be prepared by adding a minimum amount of the antifungal, antibacterial and antiviral material, thereby the productivity thereof can be increased.

Further, the object of the present invention is to provide an air cleaner having more increased trapping performance by utilizing the above-mentioned antiviral filter or antifungal, antibacterial and antiviral filter.

The another object of the present invention is to provide an air cleaner having increased life of filter by applying a stable electrical voltage.

The further object of the present invention is to provide an air cleaner which can be easily industrially prepared by limiting the amount of the concerned material to be applied to the filter to inactivate effectively viruses.

It is also an object of the present invention to provide an air cleaner with an improved virus trapping performance.

It is also envisaged in this invention to provide an air cleaner having its filter life further elongated by stabilized application of a voltage.

It is a further object of the present invention to provide an air cleaner which is capable of inactivating the trapped viruses efficiently by limiting the amount of the viruses caught on the filter and can be easily produced commercially.

It is also intended to provide an air cleaner in which the smell of tea is lessened to eliminate the unpleasant feeling of use.

A further object of the present invention is to provide an air cleaner-humidifier in which water is flown downward along the filter to improve the virus inactivating performance and to allow supply of fresh air into the room.

An additional object of the present invention is to provide an air cleaner-humidifier in which water is sprayed upward to the filter by an ultrasonic vibratory membrane to further improve the virus inactivating performance, and also water used for humidifying air is reutilized for supplying fresh air into the room.

An embodiment of the gargling cup according to the present invention for solving the above problems comprises integral attachment of a gargling agent on the cup.

Another embodiment comprises use of a tea polyphenol, which is a natural substance, as gargling agent.

Still another embodiment comprises use of a separated and purified tea polyphenol.

Yet another embodiment comprises use of a disposable material for the cup.

Further embodiment comprises impregnation of a proper amount of a gargling agent in the cup material.

Another embodiment comprises coating of a proper amount of a gargling agent on the inside surface of the cup.

Still another embodiment comprises incorporation of a gargling agent into the cup material.

Still another embodiment comprises application of a gargling agent in the form of a paste.

Still another embodiment comprises a foldable structure of the cup.

Yet another embodiment comprises wrapping or coating of a gargling agent with a water-soluble thin film.

One embodiment of the antiviral mask of the present invention for attaining said objects comprises impregnation of a tea extract in a nonwoven fabric.

Another embodiment comprises impregnation of a tea extract in an electret filter.

Still another embodiment comprises provision of a white nonwoven fabric on the front side.

Still another embodiment comprises use of a tea polyphenol prepared from a tea extract.

Yet another embodiment comprises provision of a deodorizing filter on the rear side.

Next, one embodiment of the antifungal, antibacterial and antiviral filter according to the present invention comprises applying the antifungal material, antibacterial material and antiviral material to an nonwoven fabric.

Another embodiment comprises the antibacterial and antiviral material as a tea extract.

Still another embodiment comprises at least one substance selected from epigallocatechin gallate, epicatechin gallate, epigallocatechin, epicatechin, (+) catechin and their derivatives, free theaflavin, theaflavin monogallate A, theaflavin monogallate B and theaflavin digallate as the antibacterial and antiviral material.

Another embodiment comprises an antifungal agent having low reactivity with the antibacterial agent and antiviral agent as the antifungal material.

Still another embodiment comprises a layered filter having a filter applied with an antifungal material and a filter applied with an antibacterial and antiviral material.

Yet another embodiment comprises mixing an antifungal material with an antibacterial and antiviral material and applying the mixture thereto.

Further embodiment comprises mixing a surfactant to the antifungal agent to form an antifungal material having a deliquescency.

Another embodiment comprises applying an antifungal material to a dust collector in an nonwoven fabric state and thereafter applying a tea extract which is an antibacterial and antiviral material thereto.

Still another embodiment comprises adding an antifungal material, antibacterial material and antiviral material to the dust collector.

One embodiment of the antiviral filter, air cleaner and air cleaner-humidifier according to the present invention comprises a combination of a dust collecting filter and a filter impregnated with a tea extract.

Another embodiment comprises a preliminary electric charging means.

Another embodiment comprises an electroconductive nonwoven fabric disposed in the rear of the antiviral filter.

Another embodiment comprises impregnation of a tea extract in a concentration of 0.5 g/m² or above.

Another embodiment comprises use of a dried tea extract.

Another embodiment comprises an ultrasonic vibratory membrane adapted to spray water upwardly to the filter impregnated with a tea extract.

Figure 1:
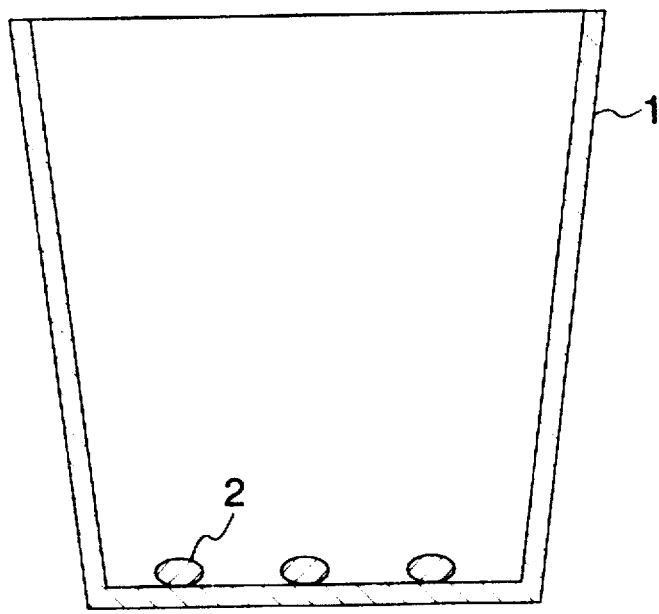
FIG. 1 is a sectional view of the cup according to Example 1 of the present invention.

The following nomenclature is used throughout the drawings:

1: cup
1a: disposable cup
1b: liquid-penetratable cup
1c: cup with a collapsible structure
2: gargling agent
2a: liquid gargling agent
2b: paste-like gargling agent
8: thin film
9: antiviral mask
10: nonwoven fabric impregnated with a tea extract
11: electret filter impregnated with a tea extract
12: white nonwoven fabric
13: deodorizing filter
14: antiviral filter
15: dust collecting filter
16: filter impregnated with a tea extract
17: antifungal, antibacterial and antiviral filter
18: antifungal agent
19: antibacterial agent
20: antiviral agent
21: antifungal filter
22: antibacterial and antiviral filter
23: antibacterial and antiviral agent
24: air cleaner
27: preliminary electric charging means
30: electroconductive nonwoven fabric
31: air cleaner-humidifier
32: dropping nozzle
33: water tank
34: water pan
35: water film
36: ultrasonic vibratory membrane

PREFERRED EMBODIMENTS OF THE INVENTION

An embodiment of the present invention comprises a cup to which a gargling agent is attached so that one can instantly obtain a liquid for gargling by merely pouring water into the cup.

Another embodiment features use of a tea polyphenol, a tea extract, as gargling agent. Being a natural extract, this gargling agent is safe to a human body and also has a prominent effect of inactivating the pathogenic viruses of cold.

Another embodiment features the fact that the tea polyphenol used as gargling agent is at least one substance selected from epigallocatechin gallate, epicatechin gallate, epigallocatechin, epicatechin, (+) catechin, their derivatives, free theaflavin, theaflavin monogallate A, theaflavin monogallate B and theaflavin digallate. The cold preventive effect of the gargling agent is elevated by specifying the tea polyphenol used as gargling agent.

Another embodiment comprises a disposable cup. This cup is handy to carry because of light weight and compact design, and it can be thrown away after use because of low price.

Another embodiment comprises a cup impregnated with a liquid gargling agent (the cup being made of a material in which liquids can penetrate). When water is poured into the cup, the gargling agent impregnated in the cup is gradually eluted into water to form a liquid for gargling. This cup can be used repetitively for gargling by merely pouring water into the cup each time.

Another embodiment comprises a cup having a gargling agent applied on its inside. When water is poured into the cup, the gargling agent applied thereon is immediately dissolved in water to an optimal concentration.

Another embodiment comprises a cup having a gargling agent incorporated therein. This cup can be produced at low cost and is capable of repetitive use and long in service life.

Another embodiment features use of a paste-like gargling agent. When water is poured into the cup, the gargling agent is immediately dissolved into water with substantially no need of stirring.

Another embodiment features a foldable cup structure. In the folded state, the cups are flat and can be carried as a compact aggregate.

Another embodiment features wrapping or coating of the gargling agent with a thin film soluble in water. Even when the cups are placed one on another, the gargling agent applied on the inside of one cup won't be transferred to the outside of another cup placed thereon.

Another embodiment comprises an antiviral mask using a nonwoven fabric impregnated with a tea extract. The viruses collected in the mask are inactivated by this medicated nonwoven fabric to prevent viral infection.

Another embodiment features use of an electret filter. The dust collecting performance of the mask is improved by the permanent charging characteristics of electret to prevent scatter of the trapped viruses, etc., in the mask.

Another embodiment features use of a white nonwoven fabric by which the proper time for change of the mask with new one is indicated definitely by discoloration the nonwoven fabric surface caused by trapping of dust by the mask.

Other embodiments feature use of a tea extract, especially a tea polyphenol, as the virus inactivating agent. This tea extract can be easily produced commercially and is potent for elevating the virus inactivating performance.

Another embodiment comprises use of a deodorizing agent by which the smell from the mask and the smell of the mask wearer's breath are eliminated.

Other embodiments feature the fact that the viruses are trapped together with dust by a dust collecting filter and inactivated by a filter impregnated with a tea extract, thereby preventing the trapped viruses from being rescattered while maintaining activity.

Another embodiment comprises an antifungal, antibacterial and antiviral filter having applied an antifungal material, antibacterial material and antiviral material to a dust collector in nonwoven fabric state, thereby air is cleaned, viral infections such as mycosis, bacterial infection and influenza is prevented.

Another embodiment comprises an antifungal, antibacterial and antiviral filter as claimed in claim 1 in which a tea extract is included as an antibacterial and antiviral material, even if the antibacterial and antiviral material is released and scattered at the production of the antifungal, antibacterial and antiviral filter or at the changing stage of the filter, such a material is not adversely influenced on a human body and the safety in work operations and in maintaining of the filter is enhanced.

Another embodiment comprises an antifungal, antibacterial and antiviral filter in which at least one substance selected from epigallocatechin gallate, epicatechin gallate, epigallocatechin, epicatechin, (+) catechin and their derivatives, free theaflavin, theaflavin monogallate A, theaflavin monogallate B and theaflavin digallate is included as an antibacterial and antiviral material, bacteria and/or viruses in dusts accumulated in the filter are effectively killed and inactivated.

Another embodiment comprises an antifungal, antibacterial and antiviral filter in which an antifungal agent which is highly compatible with the antibacterial agent and antiviral agent as an antifungal material, when said agent is adhered to cloth of a work operator, it is easily washable, the safety in work operations is enhanced and it is easy to handle it commercially.

Another embodiment comprises an antifungal, antibacterial and antiviral filter in which a filter having applied with an antifungal material and an filter having applied with an antibacterial and antiviral material are layered, fungi, bacteria and viruses are effectively trapped, a function of killing fungi and bacteria and of inactivating viruses, and a life of the filter is expanded.

Other embodiments comprise an antifungal, antibacterial and antiviral filter in which an antifungal material and antibacterial/antiviral material are mixed and the mixture is applied, application to a nonwoven fabric and the quality control are easy.

Another embodiment comprises an antifungal, antibacterial and antiviral filter by mixing a surfactant to the antifungal agent to form an antifungal material having a deliquescency, said agent is positively dissolved in dusts accumulated on the surface of the antifungal antibacterial and antiviral filter, the formation of said microorganisms on the surface of said filter is prevented, a secondary infection of fungi, bacteria and/or viruses at the changing stage of the filter or at its maintenance is prevented.

Another embodiment comprises an antifungal, antibacterial and antiviral filter in which after applying an antifungal material to a dust-collecting filter in nonwoven fabric state, a tea extract which is an antibacterial and antiviral material is applied thereto, the use of a solvent in a irreducible minimum of a demand results in an improvement of the productivity.

Other embodiments comprise an air cleaner in which viruses are trapped by a dust-collecting filter, are inactivated with a filter having a tea extract applied and rescattering of viruses while having a viable activity. Also, good economy and facilitation of quality control are assured by limiting the amount of the tea extract necessary for inactivating the viruses to be 0.5 g/m$^2$ or more.

Another embodiment comprises an air clear in which a virus-trapping performance was improved by providing a preliminary electric changing means.

Another embodiment features provision of electroconductive fibers that give uniform electric charges on the filter to elongate its service life.

In another embodiment, the flavor of the tea is reduced and odorless air is blown out from an air outlet to eliminate the unpleasant feeling due to the smell.

Other embodiments comprise an air cleaner using a tea extract polyphenol as a virus inactivating agent to facilitate commercial production of the medicated gargling cup while improving the virus inactivating performance.

Another embodiment comprises an air cleaner having an antifungal, antibacterial and antiviral performance by providing the above-mentioned antifungal, antibacterial and antiviral filter.

In an embodiment of an air cleaner-humidifier, water is flown downward along the filter to wet it, causing the tea extract to be dissolved in water to expedite inactivation of the viruses.

In an embodiment of an air cleaner-humidifier, water is sprayed upward to the filter to wet it, causing dissolution of the tea extract in water to further expedite inactivation of the viruses.

The present invention will be further illustrated by the following Examples with reference to the accompanying drawings in which like reference numerals are used to designate like parts throughout to avoid redundancy.

EXAMPLE 1

Referring to FIG. 1, there is shown a sectional view of a gargling cup 1 in accordance with a first embodiment of the present invention. As shown in the drawing, granules 2 of a gargling agent are attached to the inside surface of the cup 1 by an adhesive (not shown) such as corn syrup which is harmless to a human body.

When water is poured into the cup 1, the granular gargling agent attached to the inside of the cup 1 is dissolved into water to form a liquid for gargling, which you can directly take into your mouth for performing gargling effective for preventing cold.

Although an ordinary cylindrical cup is shown in the drawing, the cup 1 may have a handle or may be of other shapes. The cup may be made of various materials such as porcelain, resin, metal, wood, etc. Any material which is capable of holding water can produce the same effect. The cup is preferably of a shape that allows compact stacking of the cups to make it possible to carry many cups at one time. As means for attaching the gargling agent to the cup, use of an adhesive such as corn syrup was mentioned, but any other means is applicable as far as it is capable of keeping the gargling agent adhere to the cup surface.

EXAMPLE 2

Tea polyphenol, a natural tea extract, is used as gargling agent 2. Being a natural substance, this gargling agent is very high in safety and has little possibility of giving adverse effect to a human body even if this agent is used in a relatively high concentration. Further, since the tea extract has the antibacterial and antiviral activities especially against the pathogen of cold, gargling with this agent is effective for keeping off cold. Also, since the tea polyphenol can be formed into powder by drying after extraction, it can be molded into pellets and easily attached to the cup with an adhesive such as corn syrup as in the case of Example 1.

EXAMPLE 3

Separating and purifying the tea polyphenols used in the present invention, there can be obtained the catechins represented by the following formula I:

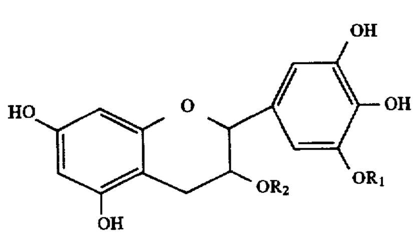

I wherein $R_1$ is H or OH, and $R_2$ is H or 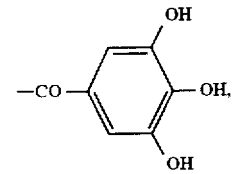 examples of these catechins including:

(−) epicatechin ($R_1$=H, $R_2$=H in the formula I);

(−) epigallocatechin ($R_1$=OH, $R_2$=H in the formula I);

(−) epicatechin gallate ($R_1$=H, 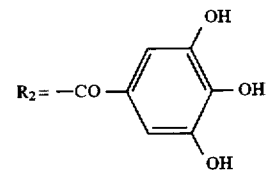 in the formula I);

(−) epigallocatechin gallate ($R_1$=OH, 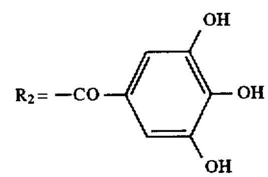 in the formula I); and the theaflavins represented by the following formula II:

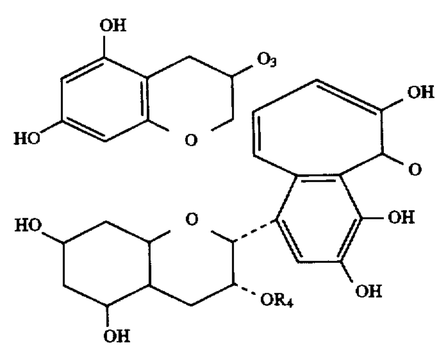

II wherein $R_3$ and $R_4$ may be same or identical and each represents H or 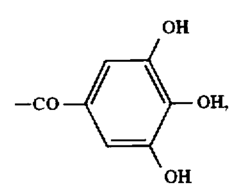 examples of these theaflavins including:

free theaflavin ($R_3$=H, $R_4$=H in the formula II);

theaflavin monogallate A

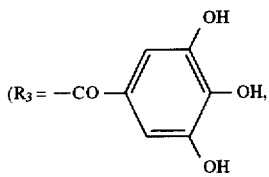

$R_4$=H in the formula II);
theaflavin monogallate B ($R_3$=H.

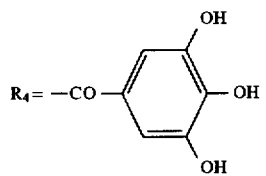

in the formula II);
theaflavin digallate

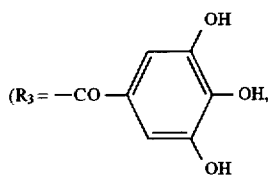

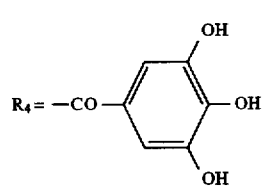

in the formula II).

The tea extracts per se contain many impurities, so their antibacterial and antiviral activities can be remarkably elevated by purifying them. Tea polyphenols can be obtained by processing the tea leaves. Examples of the processing methods and the produced compositions are shown in Patent Kokai No. 59-219384, Patent Kokai No. 60-13780, Patent Kokai No. 61-130285, etc. These tea polyphenols not only have an antibacterial activity but are also useful as an inactivating agent.

EXAMPLE 4

Figure 2:
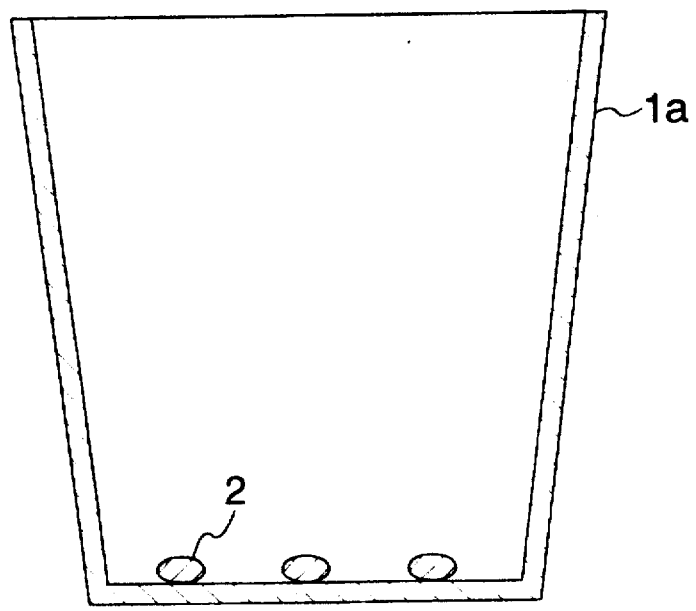
FIG. 2 is a sectional view of the cup according to Example 4 of the present invention.

A sectional view of a disposable cup 1a in accordance with the present invention is shown in FIG. 2. Since this cup 1a is substantially same as the cup 1 of FIG. 1 in structure, no detailed explanation of this cup is given here. The cup 1a is disposable after use as it is made of paper which is uncostly and poses no problem after thrown away. Generally, it is essential requisites for the disposables that they are uncostly and present no problem after thrown away. For making the product uncostly, it is tried to reduce the wall thickness and weight of the product (cup 1a in this case) itself and to device a compact design. These efforts are beneficial for making the product handy to carry.

Although paper was used as cup material in this embodiment, it is also possible to use filmy resin or metals such as aluminum foil as far as such material is uncostly, offers no problem after thrown away and also involves no difficulty in applying a gargling agent on or in the cup body.

EXAMPLE 5

Figure 3:
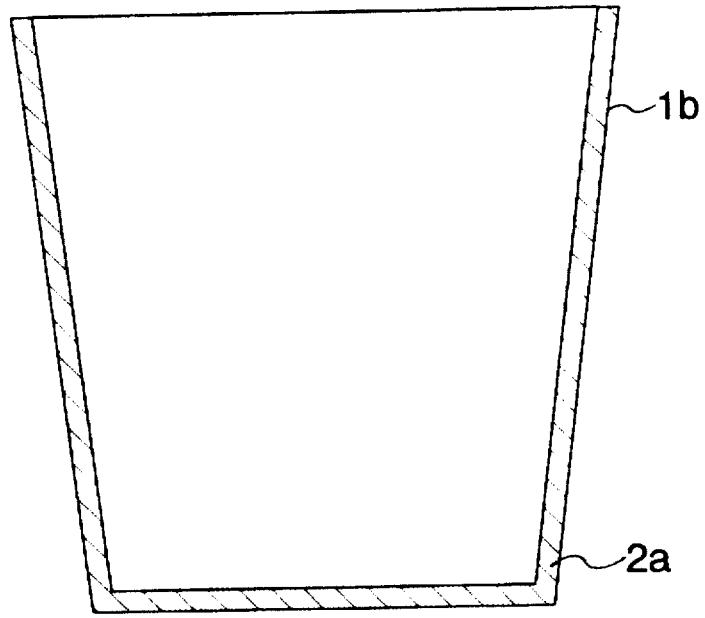
FIG. 3 is a sectional view of the cup according to Example 5 of the present invention.

FIG. 3 shows a sectional view of a cup 1b made of a material in which liquids can penetrate. In this embodiment, the cup 1b is made of pottery impregnated with a liquid gargling agent 2a.

If unglazed pottery is used as cup material, the liquid gargling agent 2a when placed in the cup 1b, penetrates spontaneously into the cup as it is porous. When the cup is then dried or calcined, the gargling agent 2a is held in the cup body in a liquid or powdery state. When water is poured into this cup, it also penetrates into the cup material, causing gradual dissolution of the gargling agent 2a into water. If the amount of the gargling agent 2a impregnated in the cup material is so controlled that a proper amount of gargling agent will be eluted out on pouring water into the cup, one can use the same cup for effective gargling as many times as the amount of the gargling agent left in the cup material permits by merely pouring water into the cup for each gargling. It is possible to prevent the gargling agent 2a from seeping out to the outside surface of the cup 1b by putting glaze on the outside surface of the cup 1b.

A cup made of unglazed pottery was illustrated as a typical example of liquid-penetratable cup according to the present invention, but the same effect can be obtained by using paper or other material as far as such material is porous and allows easy impregnation of the gargling agent. Needless to say, drying or calcination should be conducted within the temperature range which won't cause degeneration or reduction of effect of the gargling agent used.

EXAMPLE 6

Figure 4:
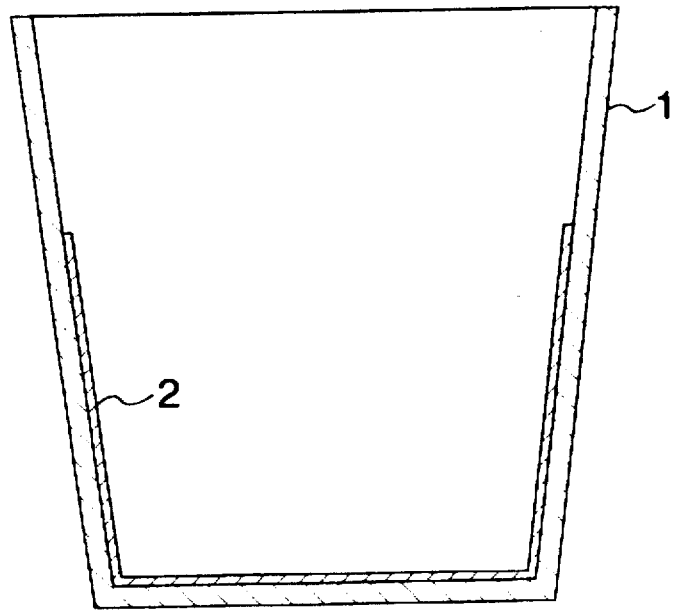
FIG. 4 is a sectional view of the cup according to Example 6 of the present invention.

Referring to FIG. 4, there is shown a sectional view of a cup 1 having a coating of gargling agent 2 on the inside surface. A uniform coating of gargling agent can be formed by dissolving a tea polyphenol (used as gargling agent) in water, brushing or spray coating the solution on the inside of the cup 1 and drying the coat.

When water is poured into this cup 1, the gargling agent 2 coated on the inside of the cup 1 is immediately contacted with and dissolved into water. Since a predetermined amount of gargling agent effective for preventing cold can be applied on the inside of the cup, it is possible to provide a garglewash with an optimal concentration of gargling agent by merely pouring water into the cup.

EXAMPLE 7

Figure 5:
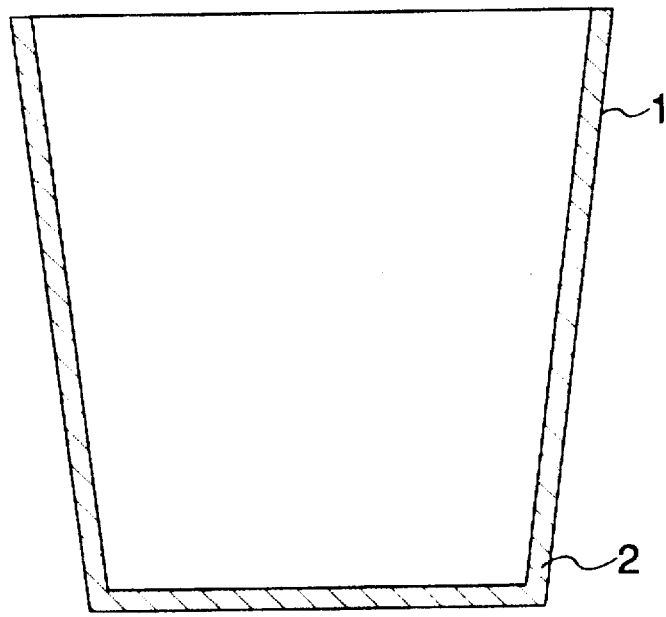
FIG. 5 is a sectional view of the cup according to Example 7 of the present invention.

A cup 1 having a gargling agent 2 incorporated in its material in accordance with the present invention is illustrated in section in FIG. 5. In this embodiment, polyethylene resin is used as cup material. A gargling agent 2 such as a tea polyphenol is mixed with the polyethylene resin in a molten state, and the mixture is placed in a mold and molded into a cup. Thereby the gargling agent 2 can be incorporated in the cup material.

When water is poured into this cup 1, the gargling agent 2 incorporated in the cup body is gradually eluted out into water. In case the gargling agent is incorporated in the cup material, the amount of the agent eluted out into water is limited, so that the optimal amount of the gargling agent to be incorporated is decided by calculating the amount of the agent incorporated and the amount eluted out into water when the latter is poured into the cup. Also, in case the gargling agent is incorporated in the cup material, since the agent is eluted out piecemeal into water, its effect is not lowered even if the cup is used for gargling a fairly large number of times by pouring water into the cup for each gargling, and thus a cup with a long service life is provided. Further, by directly incorporating the gargling agent into the cup material itself, it is possible to reduce the number of the manufacturing steps, allowing a sizable cost reduction.

In the above embodiment, polyethylene resin was used as cup material, but the same effect can be expected by using other types of resin such as polypropylene (PP), crylonitrile-butadiene-syrene (ABS), etc., paper or other materials if they are the ones in which the gargling agent can be incorporated and from which the incorporated gargling agent can be eluted out piecemeal when water is poured into the cup.

EXAMPLE 8

Figure 6:
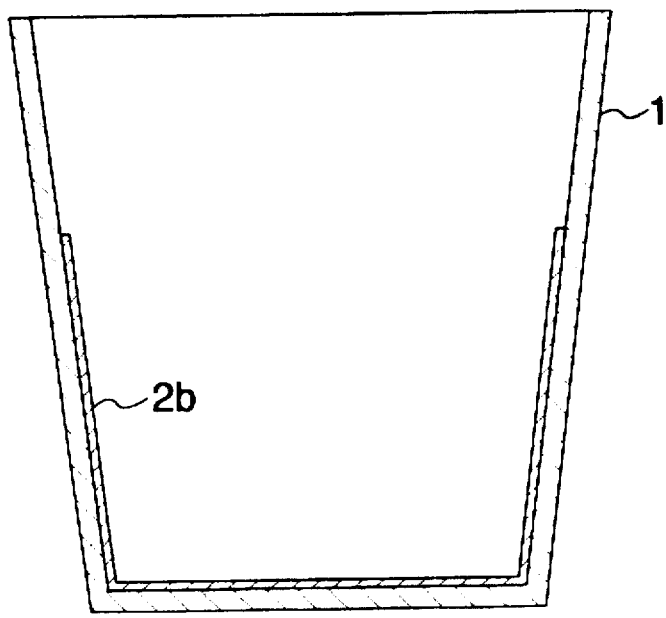
FIG. 6 is a sectional view of the cup according to Example 8 of the present invention.

A paste of gargling agent 2b is applied on the inside of a cup 1 as shown in FIG. 6.

The gargling agents such as tea polyphenols are usually in a powdery form, so that they won't be dissolved immediately when water is poured into the cup. However, if the agent is mixed with a liquid such as water to form a paste, it is fastly dissolved in water. A paste of gargling agent 2b is applied on the inside of a cup 1 in this embodiment, so that when water is poured into the cup 1, the gargling agent 2 is immediately dissolved into water to provide a garglewash with an optimal concentration of gargling agent. Thus little time is lost until the gargling agent is dissolved perfectly to provide a garglewash, and effective gargling can be performed soon after pouring water into the cup.

Usually the gargling cups are kept in a hermetically sealed state for hygientic reasons, so that even when the cups are kept in storage for a long time, the paste of gargling agent applied on the inside of the cup won't dry up and can maintain its effect.

EXAMPLE 9

Figure 7:
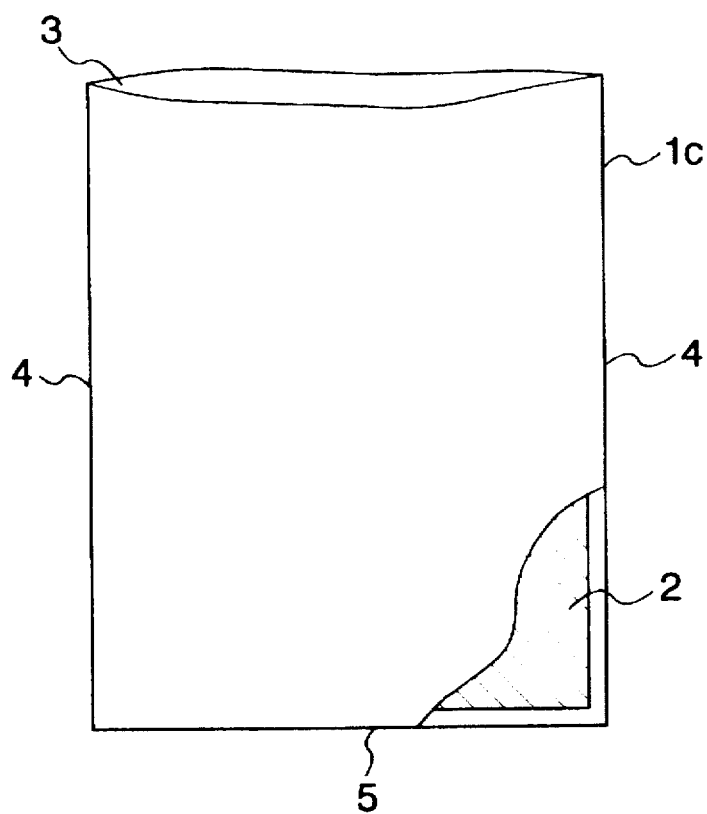
FIG. 7 is an external view of the cup according to Example 9 of the present invention.

An external view of a cup 1c of a foldable structure according to the present invention is shown in FIG. 7. The cup 1c consists of a pair of rectangular paper pieces placed one overlying the other and bonded at the sides 4 and the bottom 5, with the top end 3 being left open. A gargling agent 2 is applied on the inside of the cup 1c. The "foldable structure" refers to a structure which, when not used as a cup, is in a flattened state but, when used as a cup, can be spread out or unfolded so that it is capable of holding water.

The cup 1c is made up of a pair of rectangular pieces of paper overlapping each other, and when not used as a cup, it is in the form of a flat sheet, so that it is possible to carry many pieces of cup 1c by placing them one on another. In use of the cup 1c, the top end 3 thereof is spread out and water is poured into the cup therefrom. Water won't spill from the cup since the two paper pieces are bonded at both sides 4 and at the bottom 5. When water is poured into the cup 1c, the gargling agent 2 applied on the inside thereof is eluted out to form a liquid suited for gargling and effective for preventing cold.

Since the cups won't bulk large even if many of them are placed one on another, you can carry with you many pieces of cup when he goes out and can perform gargling anytime and anywhere you wants, specially when you go to a crowded place or a hospital where there is much opportunity of being infected with the cold viruses.

Although the cup is of a rectangular form in this embodiment, any other form will do as far as the cup is capable of holding water when it is unfolded.

Figure 8:
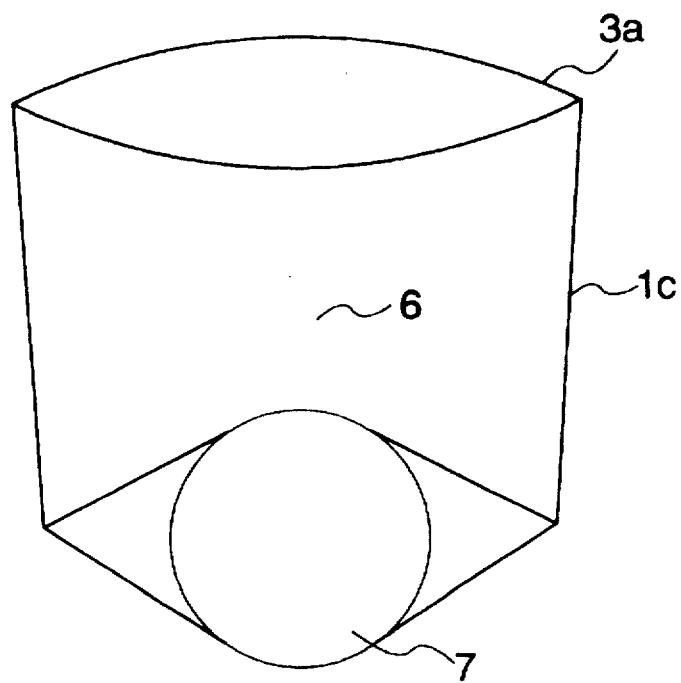
FIG. 8 is an external view of a cylindrical cup according to the present invention.

In FIG. 8 is shown the cup 1c in its collapsed state. This state is provided when both side portions 6 are flattened while the bottom portion 7 is bend up toward one side of the structure. The structure can be brought back to a cylindrical cup 1c by spreading out the top end 3a.

EXAMPLE 10

Figure 9:
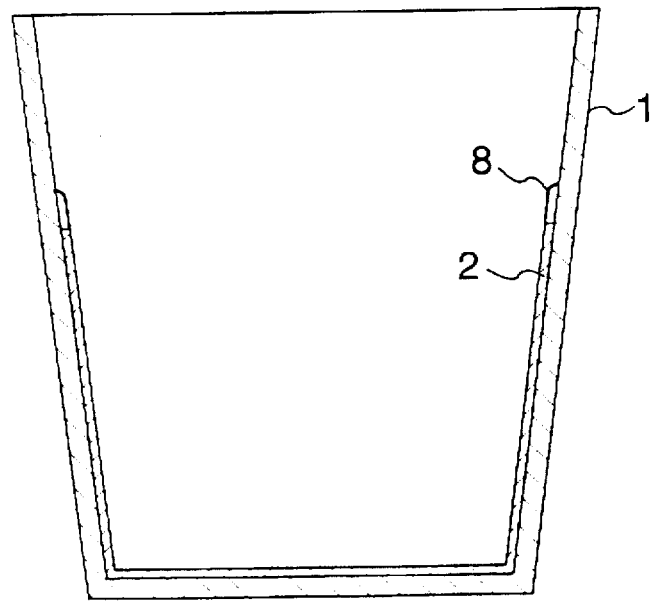
FIG. 9 is a sectional view of the cup according to Example 10 of the present invention.

A paste-like gargling agent 2b is applied on the inside of a cup 1 as shown in FIG. 9. The surface of this deposit of gargling agent 2b is covered with a thin film 8 such as a medicinal wafer which is dissolved away when contacted with water.

When water is poured into the cup 1, first the thin film 8 is contacted with water and dissolved. When the thin film 8 is dissolved away, the gargling agent 2b is now contacted with and dissolved into water to form a garglewash which is effective for preventing cold. Generally, when the cylindrical cups 1 are placed one on another, the gargling agent 2b applied on the inside of one cup may be transferred to the outside of the cup placed thereon, making it unable with this cup to form a gargle wash with an optimal concentration of gargling agent. The above embodiment of the present invention can eliminate this problem.

EXAMPLE 11

Figure 10:
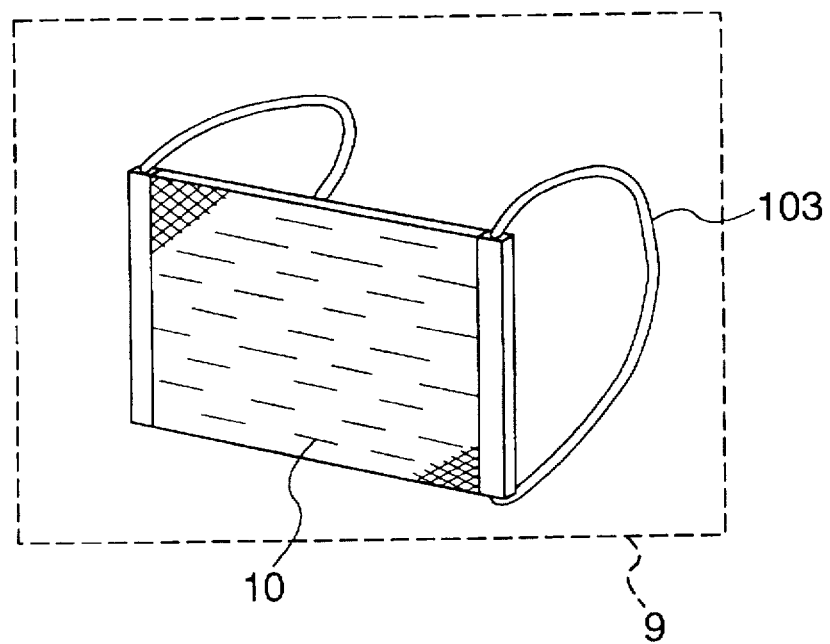
FIG. 10 is a perspective view of the antiviral mask according to Example 11 of the present invention.

An antiviral mask embodying the present invention is illustrated with reference to FIG. 10. In this and succeeding drawings, like reference numerals are used to indicate the parts identical with the conventional masks of this type, and no detailed explanation is given on such parts.

The antiviral mask 9 of this embodiment consists of a nonwoven fabric 10 impregnated with a tea extract and a pair of strings 103 to be passed round the ears.

The nonwoven fabric 10 impregnated with a tea extract was obtained by dipping a dust-collectable nonwoven fabric in a 0.1–10% aqueous solution of a tea extract obtained from green or black tea, then lightly dehydrating and finally drying said fabric.

When you wear this antiviral mask 9, the ambient air containing the influenza viruses is passed through the nonwoven fabric 10 impregnated with a tea extract as the mask wearer draws your breath. The influenza viruses carried in the air are captured by the nonwoven fabric 10 impregnated with a tea extract and thereby inactivated, allowing the clean air alone to be passed into the mask wearer's lung with breathing.

The influenza viruses trapped by the nonwoven fabric 10 are inactivated by the tea extract impregnated in the fabric. Therefore, the trapped influenza viruses are prevented from being rescattered while maintaining the infectious activity from the antiviral mask 9 and entering the mask wearer's system.

The nonwoven fabric 10 may be replaced with a filter having an equal dust collecting performance, such as high- or medium-performance filter, HEPA filter, etc.

The nonwoven fabric 10 impregnated with a tea extract may be covered with another nonwoven fabric.

For fixing the mask in position, instead of providing the strings 103 to be passed round the ears as in the conventional masks, any other suitable means may be employed as far as it can fixedly position the nonwoven fabric 10 so as to properly cover the mouth and nose of the wearer.

EXAMPLE 12

Figure 11:
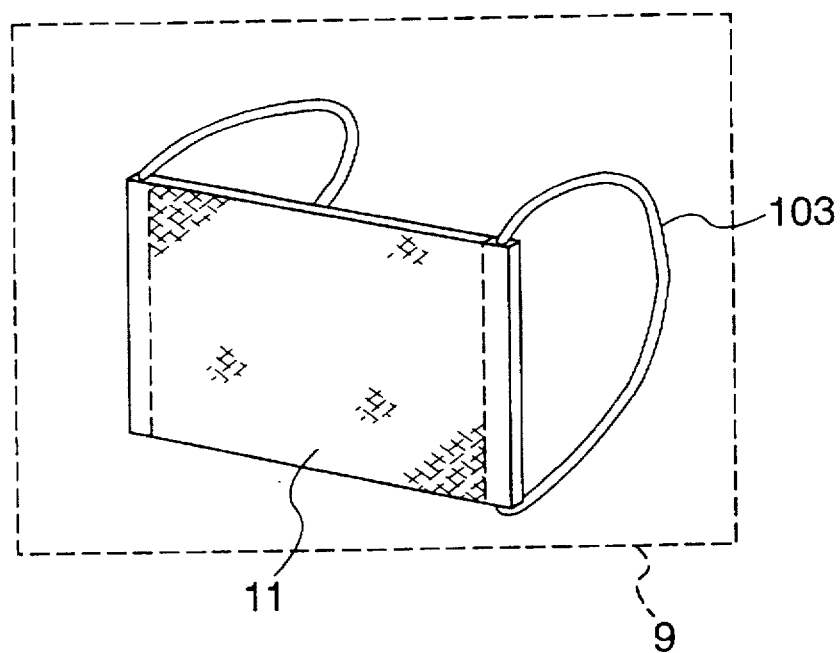
FIG. 11 is a perspective view of the antiviral mask according to Example 12 of the present invention.

In this embodiment, as shown in FIG. 11, an electret filter 11 impregnated with a tea extract is provided in place of the nonwoven fabric 10.

The influenza viruses trapped by the electret filter 11 impregnated with a tea extract are inactivated by the action of the tea extract. Therefore, the active influenza viruses are prevented from entering the mask wearer's body while maintaining infectivity from the antiviral mask 9, and thus viral infection to the mask wearer is prevented.

An advantage to the electret filter 11 is that it is lighter in weight and capable of trapping the floating dust particles at a higher efficiency than the nonwoven fabric 10 with a same thickness and a same basis weight, thus allowing efficient seizure of the viruses attached to the floating dust particles.

In a test on trapping of the viruses by the masks as measured by using a pertinent measuring device, the electret filter showed the best result in trapping the viruses.

Also, the influenza viruses let out from the mouth of a person having a cold and wearing the antiviral mask 9 are trapped by the electret filter impregnated with a tea extract and inactivated by the action of the tea extract. Thus, when a person having a cold wears the antiviral mask 9, your influenza viruses are inhibited from being transferred to other persons to prevent secondary infection of the cold.

EXAMPLE 13

Figure 12:
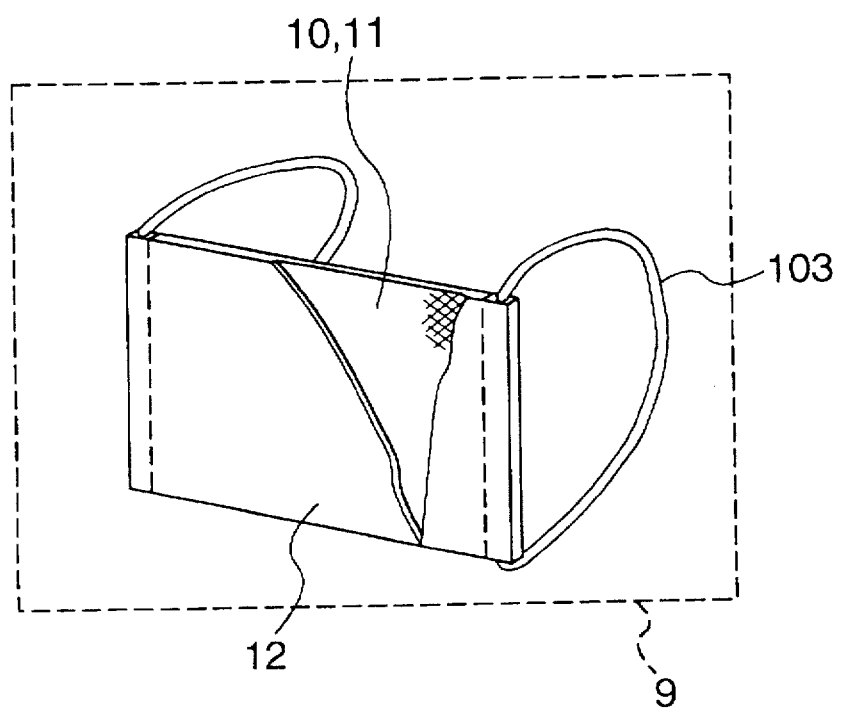
FIG. 12 is a perspective view of the antiviral mask according to Example 13 of the present invention.

This embodiment, as illustrated in FIG. 12, features laminating of a white nonwoven fabric 12 in front of the nonwoven fabric 10 or electret filter 11 impregnated with a tea extract.

Dust in the ambient air containing the influenza viruses is trapped by the white nonwoven fabric 10 with breathing of the mask wearer, and the influenza viruses are trapped and inactivated by the nonwoven fabric 10 or electret filter 11 impregnated with a tea extract, allowing the clean air alone to be sent into the mask wearer's lung.

Presence of the white nonwoven fabric 12 adds to the virus trapping performance of the antiviral mask 9, and the influenza viruses are inactivated by the tea extract in the nonwoven fabric 10 or electret filter 11 disposed behind said white nonwoven fabric 12. Thus, the influenza viruses are prevented from entering the mask wearer's body while maintaining infectivity from the antiviral mask 9.

When the nonwoven fabric 10 or electret filter 11 is impregnated with a tea extract, it is tainted with the color of the tea extract. The color of the tea extract is detrimental to the cleanliness impression, but the presence of the white nonwoven fabric 12 helps to afford the impression of cleanliness to the filter.

Various types of filter, such as electret filter, high-or medium-performance filter, HEPA filter, etc., can be used as the white nonwoven fabric 12.

EXAMPLE 14

The tea polyphenol, which is a tea extract used in the present invention, comprises at least one of the following substances: epigallocatechin gallate, epicatechin gallate, epigallocatechin, epicatechin, (+) catechin, their derivatives, free theaflavin, theaflavin monogallate A, theaflavin monogallate B and theaflavin digallate.

This tea polyphenol may be deposited on the antiviral mask 9 in the manner such as shown in Examples 11, 12 and 13 to afford a virus inactivating ability to the mask.

The tea extracts have many impurities, but a tea polyphenol, which is a purified tea extract, is capable of efficiently inactivating the influenza viruses, can be produced easily on a commercial scale and can enhance the virus inactivating performance of the antiviral mask.

EXAMPLE 15

Figure 13:
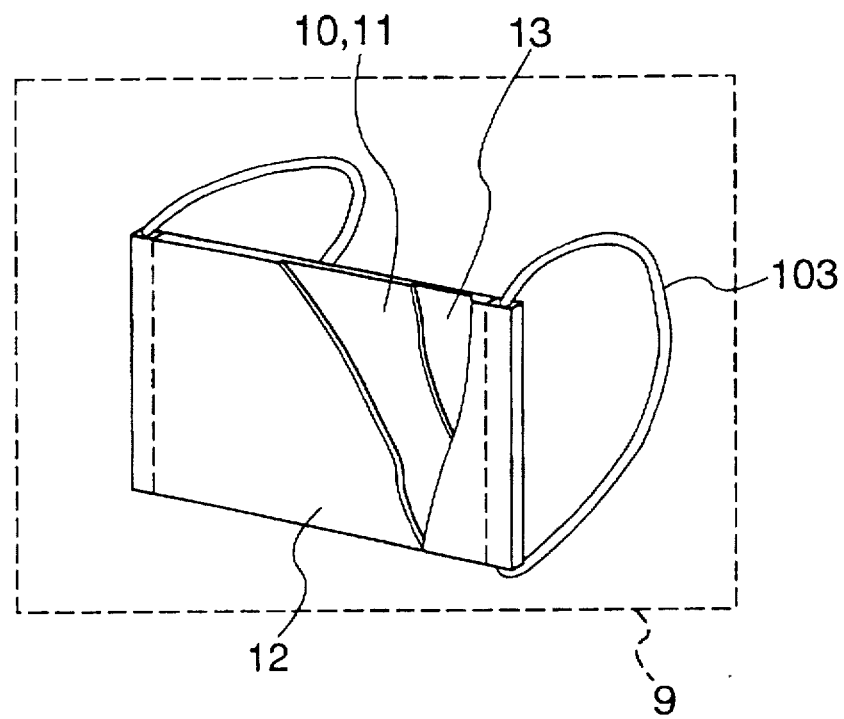
FIG. 13 is a perspective view of the antiviral mask according to Example 15 of the present invention.

As shown in FIG. 13, a white nonwoven fabric 12 and a deodorizing filter 13 are laminated in front and in the rear, respectively, of the nonwoven fabric 10 or electret filter 11 impregnated with a purified tea extract.

Dust in the ambient air containing the influenza viruses is trapped by the white nonwoven fabric 12 with breathing of the mask wearer, and the influenza viruses are trapped and inactivated by the nonwoven fabric 10 or electret filter 11 impregnated with the tea extract. The smell of the air containing the influenza viruses is eliminated by the deodorizing filter 13, thus allowing only the clean and odorless air to be sent into the mask wearer's lung.

The deodorizing filter 13 can remove the tea smell generated from the nonwoven fabric 10 or electret filter 11 impregnated with a tea extract.

EXAMPLE 16

Figure 14:
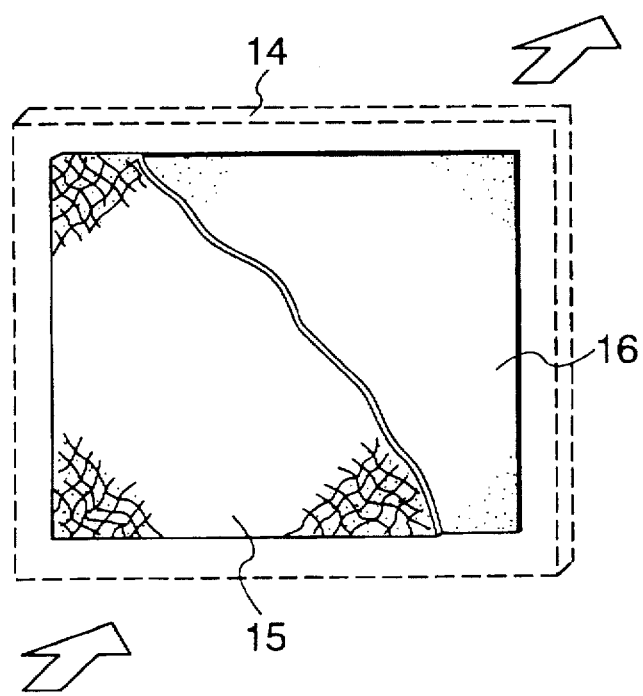
FIG. 14 is a perspective view of the antiviral filter according to Example 16 of the present invention.

This embodiment concerns an air cleaner provided with an antiviral filter 14 which, as shown in FIG. 14, comprises a laminate of a dust collecting filter 15 such as an electrically charged electret filter disposed on the upstream side and a tea extract-impregnated filter 16 disposed on the downstream side.

The filter 16 impregnated with a purified tea extract is prepared by dipping a filter having a dust collecting ability such as an electret filter in a 0.1–10% aqueous solution of a green tea or black tea extract, followed by light dehydration and final drying. The "purified tea extract" is a tea polyphenol which comprises at least one substance selected from epigallocatechin gallate, epicatechin gallate, epigallocatechin, epicatechin, (+) catechin, their derivatives, free theaflavin, theaflavin monogallate A, theaflavin monogallate B and theaflavin digallate.

The air containing the influenza viruses is sent to the antiviral filter 14 by a means such as a fan (not shown) and is cleaned by said filter 14 and released again into the room atmosphere. When the air is passed through the antiviral filter 14, the influenza viruses in the air are trapped by the dust collecting filter 15 and the filter 16 impregnated with a purified tea extract. The influenza viruses trapped by the filter 16 impregnated with a purified tea extract are inactivated by the action of the purified tea extract. In case the influenza viruses trapped by the dust collecting filter 15 are rescattered, they are again trapped and inactivated by said filter 16 disposed behind the dust collecting filter 15. Thus, the influenza viruses are inhibited from being rescattered while maintaining their activity from the antiviral filter 14, and their infection to a human body is prevented.

Generally, when an aqueous solution of a tea extract is applied to an electret filter, its virus trapping performance lowers. For maintaining the virus trapping performance, it is necessary to increase the basis weight and/or thickness of the electret filter. Also, the filter impregnated with a tea extract is tainted with a brown color by the impurities such as pigment contained in the tea extract.

These problems can be overcome by laminating the white dust collecting filter 15 in front of the filter 16 impregnated with a purified tea extract. It is thereby possible to keep the virus trapping performance, to maintain the normal white color of the filter and to judge the life of the filter by the degree of fouling on the front side of the filter.

In the embodiment shown here, an electret filter is used as the dust collecting filter 15, but the same effect can be obtained by using other types of filter such as HEPA filter, high- or medium-performance filter, bag filter, etc. However, use of an electret filter is recommended for realizing low pressure loss and high trapping rate.

An electret filter is also used as the filter 16 impregnated with a purified tea extract in the above embodiment, but the similar effect can be obtained by using an HEPA filter, high- or medium-performance filter, bag filter or the like, though an electret filter is considered best for attaining low pressure loss and high trapping rate.

EXAMPLE 17

This embodiment is explained with reference to FIG. 15.

Figure 15:
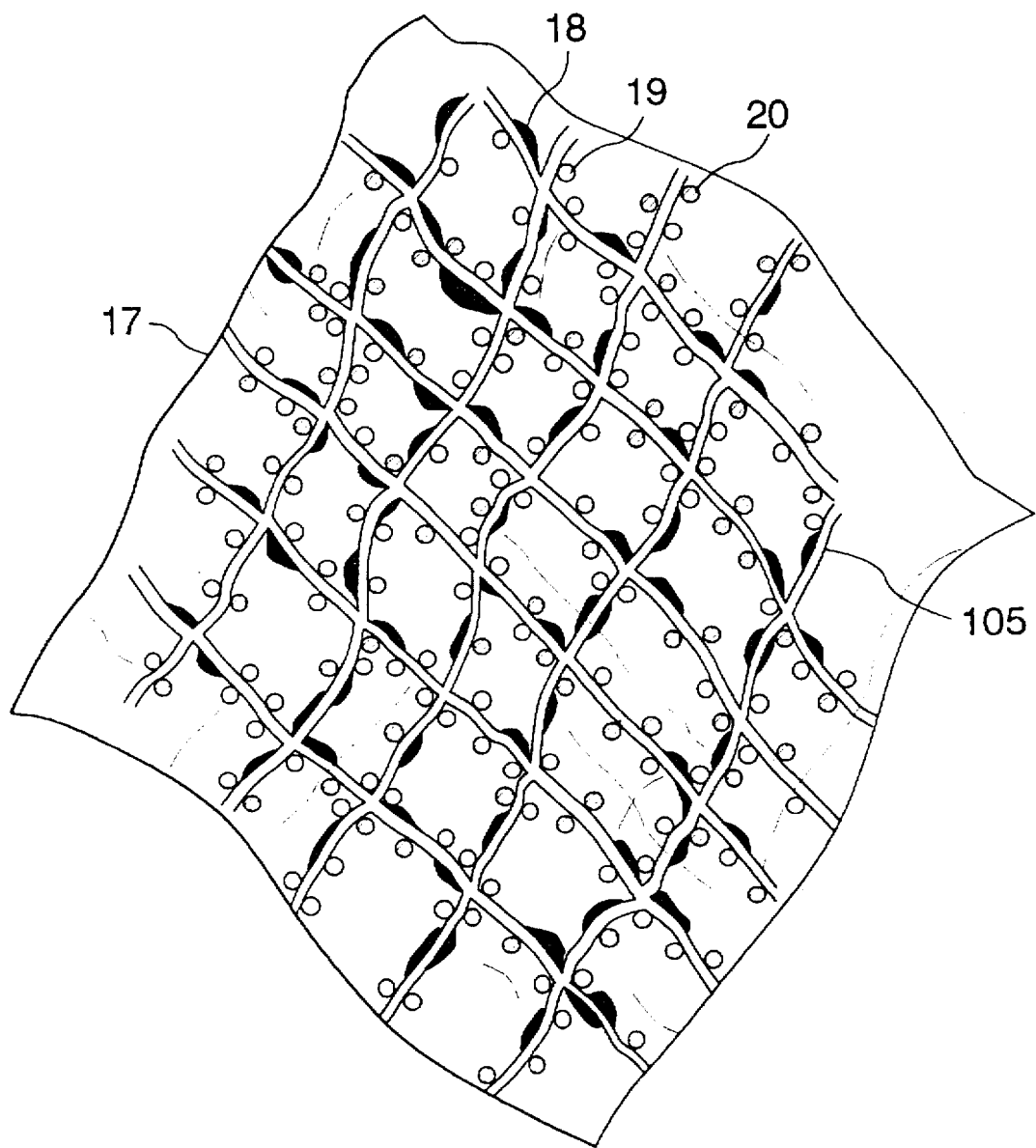
FIG. 15 is the antifungal, antibacterial and antiviral filter according to Examples 17, 18, 19, 20, 22 and 23 of the present invention.

In FIG. 15 showing a filter medium, the antifungal, antibacterial and antiviral filter 17 is provided with an antifungal agent 18, antibacterial agent 19 and antiviral agent 20 onto a nonwoven fabric 105 to kill or inactivate fungi, bacteria and/or viruses. By said constitution, the antifungal, antibacterial and antiviral filter cleans air and viral infection such as mycosis, bacterial infection and influenza is prevented.

More specifically, the antifungal material 18, antibacterial material 19 and antiviral material 20 are applied to the antifungal, antibacterial and antiviral filter 17. A benzol compound is used as the antifungal material 18, a silver-series inorganic compound as the antibacterial material 19 and flavonoids of a plant extract as the antiviral material 20.

The antifungal, antibacterial and antiviral filter 17 is prepared by applying 0.01 to 10 g/m$^2$ of silver-series inorganic compound onto the nonwoven fabric 105, thereafter dissolving a plant extract in purified water to obtain an aqueous solution of 0.1–10% by weight, dipping the fabric the solution, drying after slightly dehydrating it; thereafter dissolving the benzol compound in purified water to obtain an aqueous solution in 0.1–10% by weight, dipping said dried fabric in this solution and drying after slightly dehydrating it.

As mentioned above, the concentration of the silver-series inorganic compound is preferably 0.01 to 10 g/m$^2$. The amount of less than 0.01 g/m$^2$ results in insufficient antibacterial activity and the amount of more than 10 g/m$^2$ in lowered trapping ability of the nonwoven fabric, because said compound is covered on the nonwoven fabric of the filter and is removed from the filter.

The concentration of the benzol compound is preferably 0.1–10% by weight. The amount of less than 0.1% by weight results in poor antifungal activity and poor durability and the amount of more than 10% by weight results in formation of a bad smell from the nonwoven fabric of the filter and clogging of the filter medium, thereby the trapping ability of the nonwoven fabric is lowered.

The preferable concentration of the flavonoids is 0.1 to 10% by weight. The amount of less than 0.1% by weight results in poor antiviral activity and poor durability. The amount of more than 10% by weight results in lowered trapping ability of the nonwoven fabric, because said compound is covered on the nonwoven fabric of the filter and is removed from the filter.

The organic compound, inorganic compound and flavonoids used have preferably low reactivity when the respective compound are mixed. The effects for accerelating the killing or inactivation of fungi, bacteria and/or viruses may be obtained. For example, the organic compound possesses also an effect of inactivating a certain viruses, similarly to the case of the inorganic compound. In addition, the flavonoids have an effect of killing a certain fungi and/or bacteria.

In said constitution, the dust collecting filter unit 104 is aired using an air conditioner or fan and dirty air inside or outside a room in which fungi, bacteria and/or viruses are contained is transmitted through the antifungal, antibacterial and antiviral filter 17. Then, these microorganisms are trapped in the filter 17 to kill or inactivate them with the antifungal agent, antibacterial agent or antiviral agent attached thereto, thereby only cleaned air is transferred in the room.

The order of applying said agents is variable.

A filtering material having a trapping ability such as a medium performance filter, high performance filter, HEPA filter and electret filter may be used in the nonwoven fabric 105 of the filter 17.

Each solvent may be incorporated in a resin and the incorporated resin may be applied to the nonwoven fabric 105. A nonwoven fabric 105 may be prepared by using the incorporated resin.

There may be used an organic nitrogen/sulfur series compound, organic ester, organic iodite compound, imidazol compound, vegetable essential oils or thia benzol compound as the antifungal agent.

There may be used a zinc compound, alcohol compound, phenol compound, quaternary ammonium, benzoic acids, hydroperoxide, cresol, chlorhexidin, nitrogen-series antifungal agent, aldehydes, sorbic acid or vegetable essential oils as the antibacterial agent.

A silver compound, alcohol compound, aldehydes or vegetable essential oils may be used a the antiviral agent.

EXAMPLE 18

This embodiment is explained with reference to FIG. 15.

The antifungal, antibacterial and antiviral filter 17 of FIG. 15 showing a filter medium is provided with the antifungal agent 18, antibacterial agent 19 and antiviral agent 20 in the nonwoven fabric 105. A tea extract is used as the antibacterial agent 19 and antiviral agent 20 to kill and/or inactivate fungi, bacteria or viruses. With said constitution, the filter 17 cleans air. Even if the antibacterial and antiviral agents are released and scattered at the production of the filter or at the changing time of the filter and inhaled in mouths of the workers, there is little adversely influenced on a human body. In short, the filter has a function of improving a safety of work-operators.

More specifically, this filter 17 is comprised of a nonwoven fabric in which a tea extract such as green tea, black tea and oulong tea and antifungal material 18 have been applied.

The filter 17 may be prepared as follows: a tea extract is dissolved in purified water to obtain a solution in 0.1–10% by weight, a nonwoven fabric 105 is dipped in the solution followed by drying after slight dehydration, thereafter benzol compound is dissolved in purified water to obtain a solution in 0.1–10% by weight, the dried fabric is dipped in the solution followed by drying after slight dehydration.

The concentration of the tea extract is preferably 0.1–10% by weight. The amount of less than 0.1% by weight results in reduced antibacterial and antiviral activities and poor durability of the filter. The amount of more than 10% by weight results in reduced trapping ability, because said extract is covered on fibers of the nonwoven fabric and is removed from the filter.

The concentration of the benzol compound is preferably 0.1–10% by weight. The amount of less than 0.1% by weight results in lowered antifungal activity and the durability of the filter. The amount of more than 10% by weight results in formation of bad smell from the fabric and clogging of the filter medium, thereby the trapping ability of the nonwoven fabric is lowered.

Said tea extract possesses antiviral activity and is sensitive to a general bacteria such as E. Coli and S. Aureus. Hence, the antibacterial and antiviral activities may be added simultaneously without use of a silver-series inorganic compound by applying it to the nonwoven fabric 105. Said extract, which is a natural substance, may be easily prepared with a commercial scale and is not harmful to a human body. Accordingly, even if the extract is released from the fabric at the processing stage of the filter, highly safe filter may be provided.

EXAMPLE 19

This embodiment is explained with reference to FIG. 15.

In FIG. 15 showing a filter medium, the antifungal, antibacterial and antiviral filter is provided with an antifungal agent 18, antibacterial agent 19 and antiviral agent 20 onto a nonwoven fabric 105. There may be used at least one substance selected from epigallocatechin gallate, epicatechin gallate, epigallocatechin, epicatechin, (+) catechin and their derivatives, free theaflavin, theaflavin monogallate A, theaflavin monogallate B and theaflavin digallate as the antibacterial agent 19 and antiviral agent 20 to kill or inactivate fungi, bacteria and/or viruses. With said constitution, the filter has functions of cleaning air, effectively killing and inactivating these microorganisms within dusts accumulated on the filter.

More specifically, the antifungal, antibacterial and antiviral filter 17 is constituted of at least one substance selected from epigallocatechin gallate, epicatechin gallate, epigallocatechin, epicatechin, (+) catechin and their derivatives, free theaflavin, theaflavin monogallate A, theaflavin monogallate B and theaflavin digallate which has been separated and purified from green tea or black tea as the antibacterial and antiviral agents and a nonwoven fabric in which the antifungal material 18 has been applied.

This filter may be prepared as follows: a tea extract separated and purified from green tea or black tea is dissolved in purified water to obtain a solution in 0.05–5% by weight, a nonwoven fabric 105 is dipped in the solution followed by drying after slight dehydration, thereafter benzol compound is dissolved in purified water to obtain a solution in 0.1–10% by weight, and the dried fabric is dipped in the solution followed by drying after slight dehydration.

The concentration of the tea extract is preferably 0.05–5% by weight. The amount of less than 0.05% by weight results in reduced antibacterial and antiviral activities and poor durability of the filter. The amount of more than 5% by weight results in reduced trapping ability of the filter.

The tea extract separated from the green tea or black tea contains impurities and is preferably purified to a tea polyphenol. Thereby, it can effectively kill or inactivate bacteria or viruses. The tea polyphenol has a high deliquescency and can enhance the killing or inactivation of bacterial/viruses in dusts, thereby cleaned air in which the microorganisms have been removed can be obtained from air conditioner.

EXAMPLE 20

This embodiment is explained with reference to FIG. 15. In FIG. 15 showing a filter medium, the antifungal, antibacterial and antiviral filter 17 is provided with the antifungal agent 18, antibacterial agent 19 and antiviral agent 20 onto the nonwoven fabric 105 to kill or inactivate fungi, bacteria and/or viruses.

With said constitution, the filter 17 cleans air. When said agents are adhered to the work-processor, it is easy to wash them. Thus, the safety of the processor may be increased.

More specifically, the filter 17 is composed of the antifungal material 18, antibacterial and antiviral agents, highly dispersible benzol compound and a nonwoven fabric having the benzol compound and said agents applied.

The antifungal, antibacterial and antiviral filter 17 may be prepared as follows: a tea extract, which has been separated and purified from green tea or black tea, is dissolved in purified water to obtain a solution in 0.05–5% by weight, nonwoven fabric 105 is dipped in the solution followed by drying after slight dehydration, thereafter a benzol compound is dissolved in purified water to obtain a solution in 0.1–10% by weight, the dried fabric is dipped in the solution followed by drying after slight dehydration.

By highly dispersible antifungal agent is meant one in which emulsification or coagulation does not occur in mixing with an antibacterial agent or antiviral agent. Additionally, it refers to one which may prevent from the formation of bad smell from the nonwoven fabric and is difficult to injure fibers of the filter.

The use of the above-mentioned antifungal agent having a low reactivity can effectively kill fungi and there may be provided the filter which is superior in industrial processability and is easily produceable.

Thiabenzol solvent which has been generally utilized may be used. This highly dispersible antifungal agent has preferably a low reactivity with the antibacterial and antiviral agents and does not reduce the effects of each solvent.

EXAMPLE 21

Figure 16:
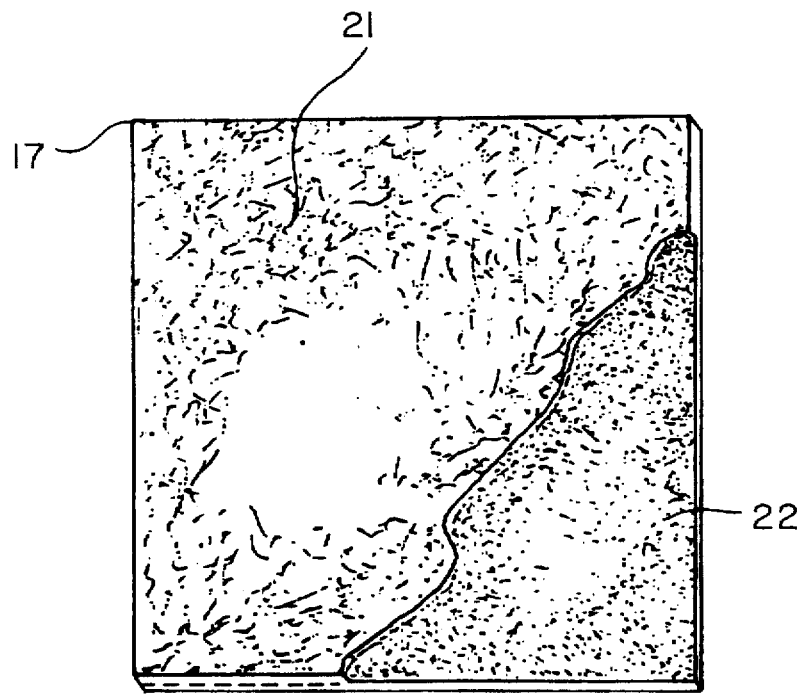
FIG. 16 is the antifungal, antibacterial and antiviral filter according to Example 21 of the present invention.

This embodiment is explained with respect to FIG. 16.

In FIG. 16 showing a structure of a filter, the filter 17 is comprised of a layer of an antifungal filter 21 in which an antifungal material has been applied to nonwoven fabric 105 and an antibacterial/antiviral filter 22 in which an antibacterial and antiviral material has been applied thereto, thereby these microorganisms are killed or inactivated.

With said constitution, the filter 17 effectively traps fungi, bacteria or viruses to increase the killing activity of fungi/bacteria and the inactivation activity of viruses. Additionally, the shelf life of the filter may be extended.

More specifically, the filter 17 is comprised of a layer of an antifungal filter 21 in which an antifungal material 18 has been applied to an open nonwoven fabric (medium performance filter or high performance filter) and then the drying thereof been effected; and an antibacterial/antiviral filter 22 in which an antibacterial material 19 and antiviral material 20 have been applied to a fine nonwoven fabric and then the drying been effected.

A benzol compound is used as the antifungal material 18 and a tea extract separated and purified from black tea is used as the antibacterial material 19 and antiviral material 20.

The antifungal filter 21 is a filter obtained by applying 0.1–10% by weight of a benzol compound and drying. The antibacterial/antiviral filter 22 is a filter obtained by applying an antibacterial/antiviral agent to a fine nonwoven fabric (high performance filter or HEPA, ULPA) and then drying.

The antifungal, antibacterial and antiviral filter 17 comprises the antifungal filter 21 in a front phase and the antibacterial/antiviral filter 22 in a rear phase to air to be transmitted.

With said constitution, dirty air inside or outside a room in which fungi, bacteria and/or viruses are contained is transmitted through the antifungal, antibacterial and antiviral filter 176. At this time, fungi are trapped in the antifungal filter 21 of the front phase and killed, and bacteria and viruses are trapped in the antibacterial and antiviral filter 22 and killed or inactivated.

In general, fungi have a diameter of 0.5 µm or more, bacteria and viruses have a diameter of 0.01–0.8 µm. In view of different diameter, for example, it is considered that the nonwoven fabric of the front phase in which the antifungal agent has been applied is used as medium performance filter and high performance filter, and the nonwoven fabric of the rear phase in which the antibacterial and antiviral agents have been applied is used as high performance filter, HEPA filter and ULPA filter.

The trapping ability of fungi, bacteria and viruses in the antifungal, antibacterial and antiviral filter 1 may be improved, the microorganisms may be exactly killed or inactivated, the trapping ability of the antifungal, antibacterial and antiviral filter 17 may be strengthened and the changing time thereof may be extended.

EXAMPLE 22

This embodiment is explained with reference to FIG. 15.

In FIG. 15 showing a filter medium, the antifungal, antibacterial and antiviral filter 17 is provided with an antifungal agent 18, antibacterial agent 19 and antiviral agent 20 onto a nonwoven fabric 105 and may be prepared by mixing these agents 18, 19 and 20 and applying the mixture to the nonwoven fabric 105, thereby these microorganisms are killed or inactivated.

With said constitution, the filter 17 cleans air, application of the nonwoven fabric is easy and the quality control thereof may be simply effected.

More specifically, the filter 17 may be prepared as follows: each aqueous solution of benzol compound in 0.1–1% by weight and of antibacterial/antiviral agent in 0.1–10% by weight is prepared, nonwoven fabric is dipped in the solution followed by drying after slight dehydration. The benzol compound and the antibacterial/antiviral agent have a low reactivity and they can be mixed at the application stage.

With said constitution, fungi, bacteria and/or viruses may be trapped by the nonwoven fabric, be killed or inactivated, and the antifungal, antibacterial and antiviral abilities may be simultaneously incorporated in the nonwoven fabric. Thus, the present invention may be provided with the costly low filter which is easily prepared industrially.

These agents may be mixed together with any dispersing agent.

EXAMPLE 23

This embodiment is explained with reference to FIG. 15.

In FIG. 15 showing a filter medium, this filter 17 is provided with an antifungal agent 18, antibacterial agent 10 and antiviral agent 20 together with a surfactant as not shown onto nonwoven fabric 105 to kill or inactivate fungi, bacteria or viruses.

With said constitution, the filter 17 cleans air, includes accumulated dusts positively, prevents from the formation of these microorganisms on the surface of the filter and prevent from secondary invention thereof at the changing time of the filter or at the maintenance time.

More specifically, a tea extract from green tea or black tea is more dispersible in the presence of the benzol compound and the surfactant. Additionally, the deliquescency of the tea extract is imparted to the benzol compound to obtain a high deliquescent antifungal material.

This antibacterial and antiviral filter may be prepared as follows: 0.1–10% by weight of benzol compound and the tea extract from green tea or black tea is dissolved in purified water, a solution of 0.05–5% by weight of the tea extract and 0.015 by weigh or more of a surfactant is prepared, nonwoven fabric is dipped in the solution followed by drying after slight dehydration.

With said constitution, when a air conditioner is run for a long time, the antifungal agent, antibacterial agent and antiviral agent may from out the filter to kill or inactivate the microorganisms within dust accumulated on the surface of the filter. Hence, there may be provided the antifungal, antibacterial and antiviral filter which can maintain high killing or inactivation abilities and can extend the changing time of the filter.

The surfactant may be a solvent which may improve the dispersibility of the antifungal agent and be one which can improve the dispersibility of the antibacterial agent and antiviral agent.

EXAMPLE 24

This embodiment is explained with reference to FIG. 17.

Figure 17:
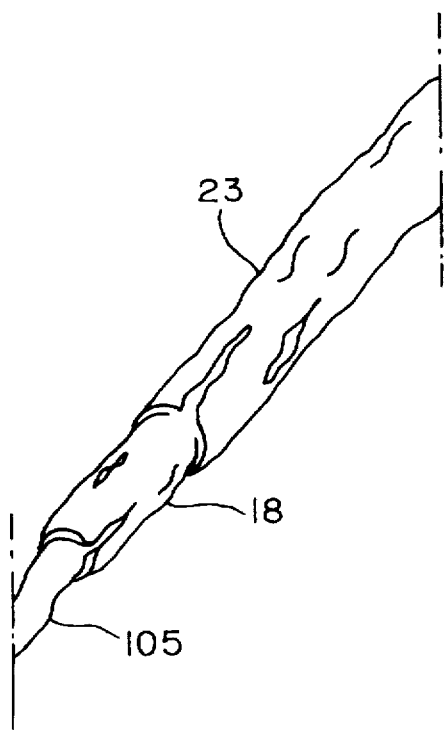
FIG. 17 is a structural drawing of the antifungal, antibacterial and antiviral filter according to Example 24 of the present invention.

In FIG. 17 showing a filter medium, the filter 17 is applied with the antifungal agent 18 on the surface of the nonwoven fabric 105 and is provided with the antibacterial and antiviral agents on the surface of the antifungal agent to kill or inactivate fungi, bacteria and viruses.

With said constitution, said filter 17 cleans air and the productivity thereof may be increased by using solvent in minimum limit of need.

More specifically, the filter 17 may be prepared as follows: an aqueous solution of benzol compound in 0.1–10% by weight which is the antifungal material 18 is applied to the nonwoven fabric filter medium 105, thereafter the nonwoven fabric 105 is dipped in 0.1–10% by weight solution of a tea extract which is the antibacterial and antiviral material 23 followed by drying after slight dehydration.

With said constitution, the antibacterial and antiviral material 23 is adhered to the upper surface of the antifungal material 18 which has been adhered to the nonwoven fabric filter medium 105, fungi adhered to the antibacterial and antiviral material 23 is killed with the antifungal material 18 which is in the lower portion of the antibacterial and antiviral material 23 and bacteria and viruses are killed or inactivated with the antibacterial and antiviral material 23. In general, fungi has a diameter of 0.5 µm or more and bacteria and viruses have a diameter of 0.01–0.8 µm. Fungi may be easily trapped in the nonwoven fabric filter medium and the rate contacted with the nonwoven fabric becomes larger. Accordingly, it is necessary to broaden the rate to be contacted with the antibacterial and antiviral agent. When the antibacterial and antiviral material 23 is applied to the nonwoven fabric, after applying the antifungal material 18 thereto, the contacting rate of bacteria or viruses is increased and the contact of fungi may be assured.

By firstly applying the antifungal material 18 to the nonwoven fabric, the antibacterial and antiviral material 23 on the nonwoven fabric get intimate and the amount of the materials to be applied to the nonwoven fabric may be minimum limit.

EXAMPLE 25

Figure 18:
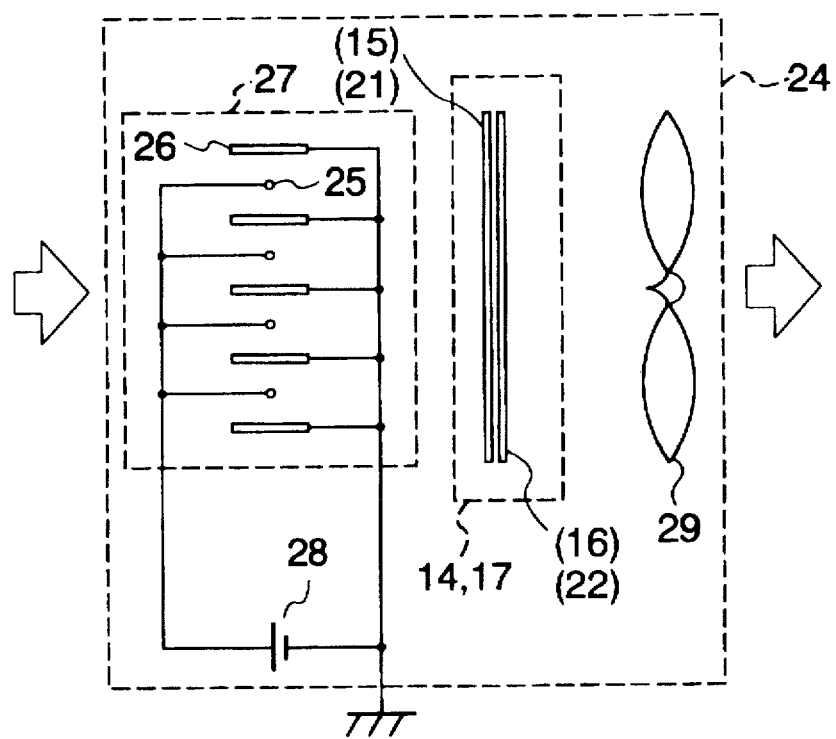
FIG. 18 is a sectional view of the air cleaner according to Example 25 of the present invention.

Referring to FIG. 18, the invention is embodied as an air cleaner 24 featuring provision of a preliminary electrical charging means 27 comprising combinations of discharge wires 25 and earth plates 26, said means being disposed upstream of the antiviral filter 14 or the antifungal, antibacterial and antiviral filter 17. A DC voltage of 3–5 kV/cm is applied to said discharge wires 25 and earth plates 26 from a power source. A fan 29 is provided downstream of the antiviral filter 14 or the antifungal, antibacterial and antiviral filter 17.

The air containing the influenza viruses and dust particles in the room is brought to the preliminary charging means 27 by the fan 29. Corona discharge is induced in said preliminary charging means 27 as a DC voltage is applied thereto. The influenza viruses and dust particles in the air supplied to said charging means 27 are charged positively due to said corona discharge. The charged influenza viruses and dust particles are captured by the antiviral filter 14 or the antifungal, antibacterial and antiviral filter 17 and the cleaned air is released into the room from the air cleaner 24 by the fan 29.

The influenza viruses are inactivated as they pass through the area of corona discharge. Thus, by providing the preliminary charging means 27 upstream of the antiviral filter 14 or the antifungal, antibacterial and antiviral filter 17, the load on said antiviral filter or the antifungal, antibacterial and antiviral filter 17 is lessened, resulting in an enhanced influenza virus trapping performance of the filter.

EXAMPLE 26

Figure 19:
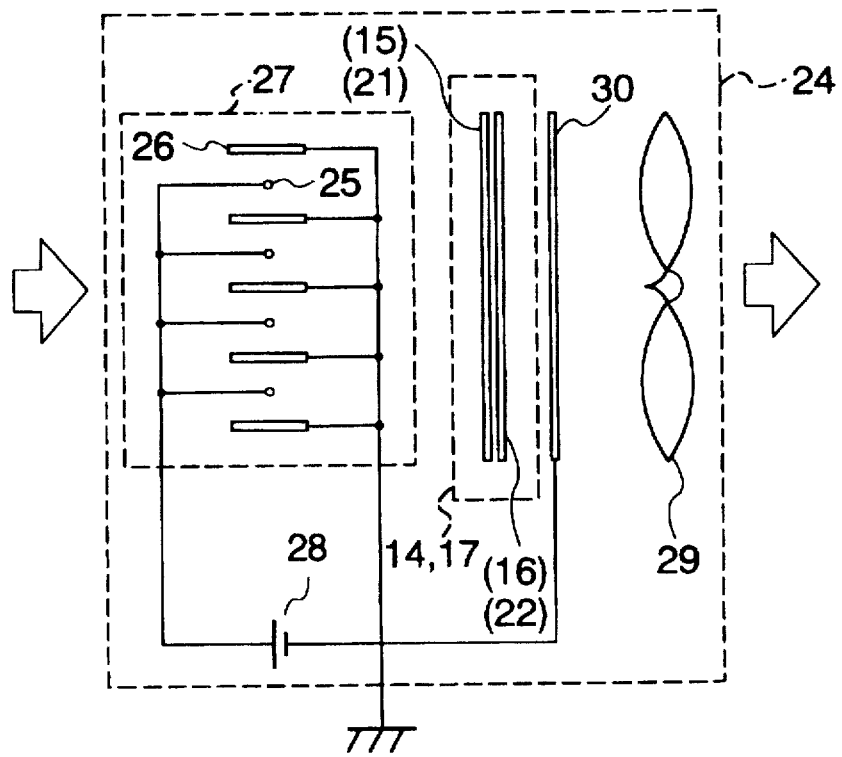
FIG. 19 is a sectional view of the air cleaner according to Example 26 of the present invention.

A similar air cleaner is provided as shown in FIG. 19, in which the parts same as those in Example 25 are assigned the like reference numerals to avoid redundancy.

In this embodiment, as shown in FIG. 19, an electroconductive nonwoven fabric 30 is provided downstream of the antiviral filter 14 or the antifungal, antibacterial and antiviral filter 17 in close attachment thereto and connected to the minus side of the power source 28.

An electric field is created between the discharge wire 25 and the electroconductive nonwoven fabric 30 as a DC voltage is applied thereto from the power source 28. The antiviral filter 14 or the antifungal, antibacterial and antiviral filter 17 is reduced in charging performance, resulting in lowered trapping performance, as it traps the influenza viruses and dust particles. However, as the antiviral filter 14 or the antifungal, antibacterial and antiviral filter 17 is disposed in the electric field, it becomes electrically charged to restore the charging performance and also allow generation of uniform charge.

Thus, the influenza virus and dust particle trapping performance of the antiviral filter 14 or the antifungal, antibacterial and antiviral filter 17 is enhanced and its service life is prolonged as its trapping performance can be maintained for a long time.

Since the filter 16 or the antibacterial and antiviral filter 22 impregnated with a purified tea extract is sandwiched between the dust collecting filter 15 or the antifungal filter 21 and the electroconductive nonwoven fabric 30, the possibility of its being deformed by air blast is reduced to minimize the risk of release or rescatter of the tea extract, resulting in an elongated service life. The trapped influenza viruses and dust particles are also prevented from being rescattered.

EXAMPLE 27

The influenza viruses trapped by the dust collecting filter such as electret filter can be inactivated positively and efficiently by defining the amount of the tea extract applied to the filter to be 0.5 g/m$^2$ or greater. Also, the antiviral filter of this embodiment can be applied to the air cleaner of Example 25 or 26 without raising any problem.

Figure 20:
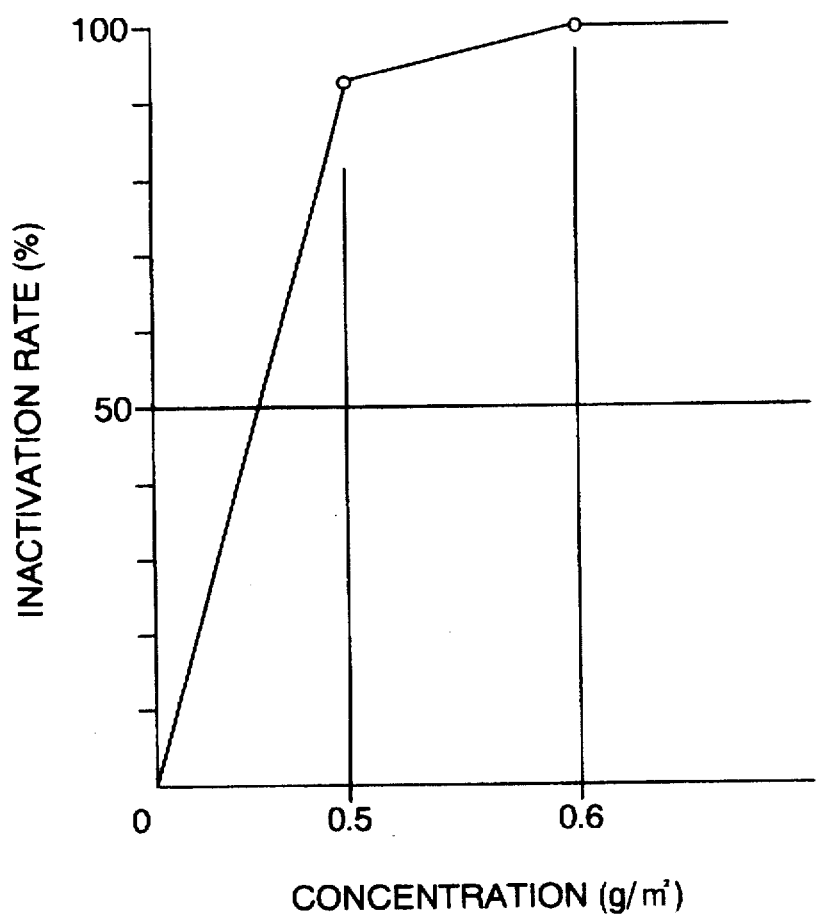
FIG. 20 is a performance graph of the tea extract impregnated in the filter according to Example 27 of the present invention.

There is a relationship such as graphically shown in FIG. 20 between the applied amount of the tea extract and the influenza virus inactivation rate, which indicates that 0.5 g/m$^2$ or a greater amount of the tea extract is necessary for inactivating 99% of the influenza viruses trapped by the antiviral filter.

Also, by determining the minimal requirement of tea extract for inactivating 99% of the trapped influenza viruses, it is possible to minimize the error in design and to maintain performance of the antiviral filter 14, thus facilitating the quality management.

EXAMPLE 28

The tea extract obtained from green or black tea retains the smell of tea. Therefore, when such a tea extract is applied as it is to the filter, the filter smells of tea, and when air is passed through the filter, it is loaded with a smell of tea and lets out its smell when discharged from the air outlet.

Since the smell of tea comes from volatile matter, this smell can be lessened substantially by drying the tea extract at 100° C. for 1–24 hours.

The same effect can be obtained by drying the tea extract after it has been applied to the filter.

Among the tea extracts, tea polyphenols having influenza virus inactivating ability are subject to oxidative destruction when dried at a temperature above 100° C., resulting in reduced active ingredient. But when they are dried at a temperature below 100° C., there takes place no oxidative destruction and the smell matter alone is volatized. Therefore, it is possible to reduce the odor density while maintaining the influenza virus inactivating effect, and the air let out from the air outlet can be made odorless, eliminating the unpleasant feeling of smell.

EXAMPLE 29

Figure 21:
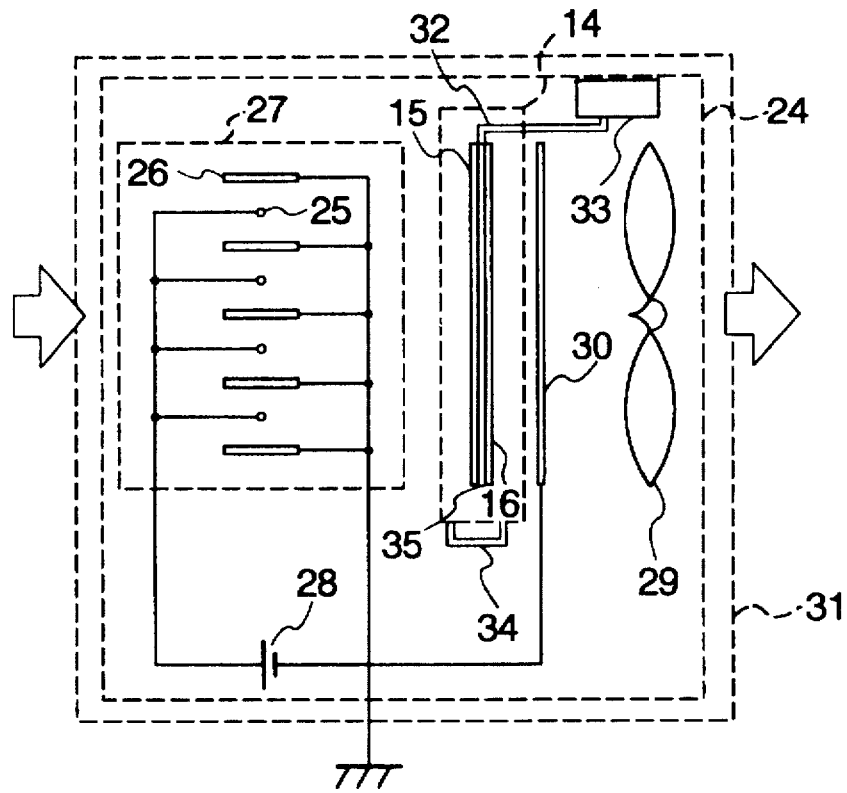
FIG. 21 is a sectional view of the air cleaner-humidifier according to Example 29 of the present invention.

An air cleaner-humidifier in accordance with the present invention is illustrated with reference to FIG. 21.

In the body of the air cleaner-humidifier 31 is provided a preliminary charging means 27 consisting of discharge wires 25 and earth plates 26, said charging means being disposed upstream of an antiviral filter 14. A dropping nozzle 32 and a water tank 33 are provided above said antiviral filter 14, and a water pan 34 is provided below said filter 14. A DC voltage of 3–5 kV/cm is applied across said discharge wires 25 and earth plates 26 from a power source 28. A fan 29 is provided downstream of said antiviral filter 14.

Water tank 33 contains water to be used for supplying moisture into the room. Water from the tank 33 is atomized and sprayed to the antiviral filter 14 from the dropping nozzle 32 to form a water film 35. Superfluous water is received by the water pan 34 and discharged out of the system.

It is known that the influenza virus inactivating performance of the filter 16 impregnated with a tea extract drops proportionally as dust is trapped and accumulated in the filter 14. As moisture is given to the tea extract-impregnated filter 16 from top of the antiviral filter 14, such moisture transfers to the trapped dust. The tea extract has the nature that it is easily dissolved in water.

The influenza viruses attached to the moistened dust particles become more liable to contact with the tea extract eluted from the filter 16, resulting in an increased influenza virus inactivating performance of the filter and an improvement of its durability.

Further, the water film 28 allows formation of a more uniform electric field and also serves for giving moisture in the air passed therethrough to the dust particles. This encourages the protective effect against cold which tends to spread in dry atmosphere, and is also helpful for supplying clean and fresh air into the room.

EXAMPLE 30

Figure 22:
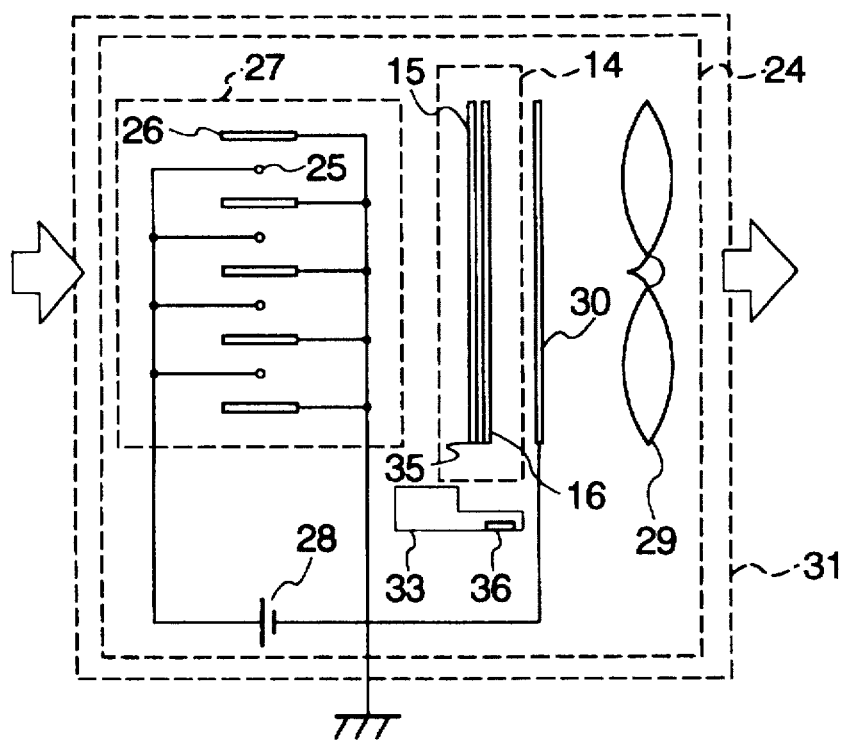
FIG. 22 is a sectional view of the air cleaner-humidifier according to Example 30 of the present invention.
Figure 23:
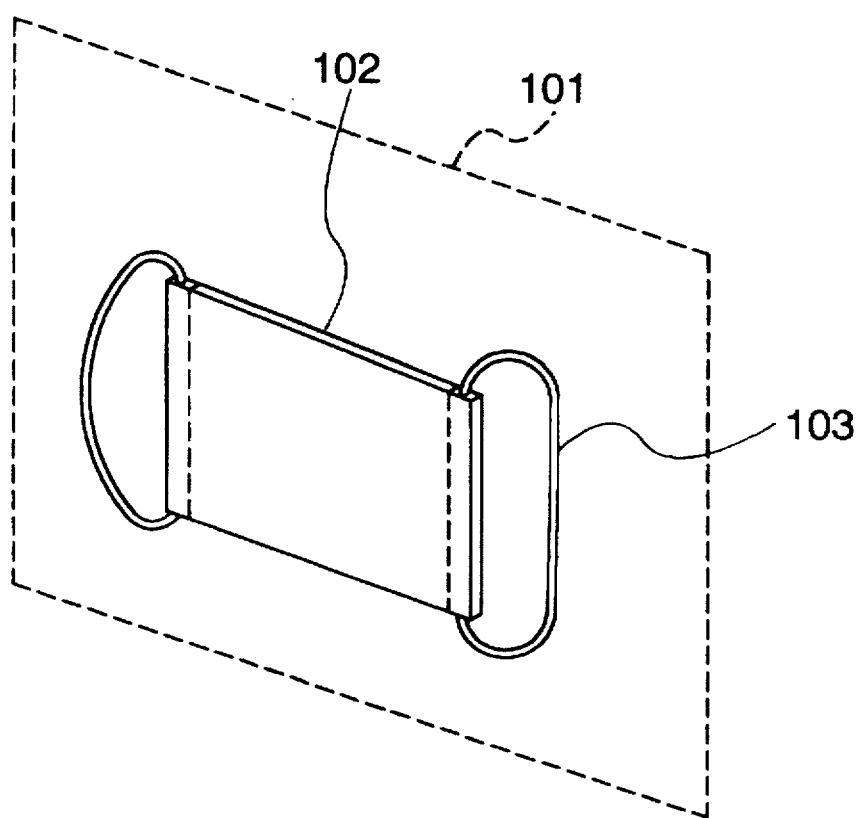
FIG. 23 is a perspective view of a conventional mask.
Figure 24:
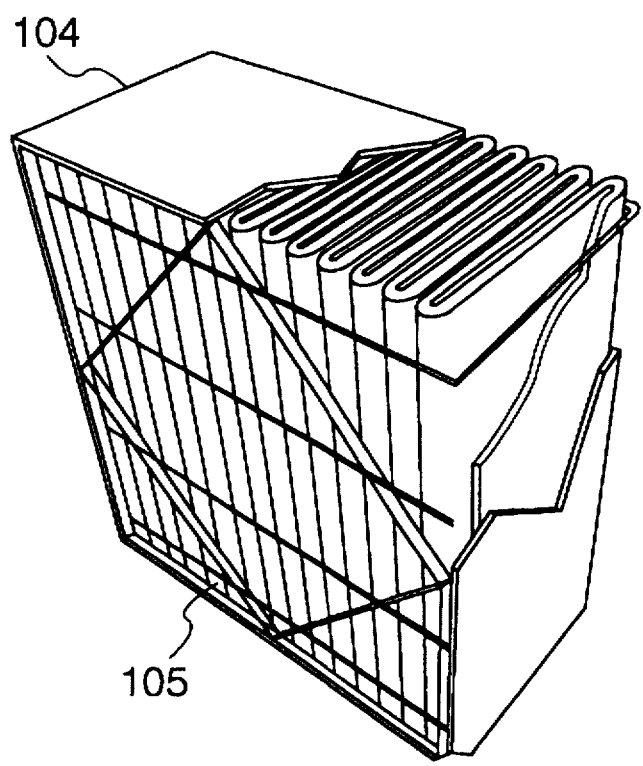
FIG. 24 is a schematic drawing showing a structure of a conventional dust collecting filter.

In the air cleaner-humidifier 31 according to this embodiment, as shown in FIG. 22, a preliminary charging means 27 consisting of discharge wires 18 and earth plates 19 is provided upstream of an antiviral filter 14, and a water tank 33 and an ultrasonic vibratory membrane 36 are provided below said antiviral filter 14. A DC voltage of 3–5 kV/cm is applied across said discharge wires 25 and earth plates 26 from a power source 28. A fan 29 is provided downstream of the antiviral filter 14. Said fan 29 and ultrasonic vibratory membrane 36 are energized by the power source 28.

In the water tank 33 is contained water for supplying moisture into the room. This water is also used for humidifying the antiviral filter 14 and forming a water film 35 by operating the ultrasonic vibratory membrane 36. Superfluous water is returned to the water tank 33 for reuse.

It is known that the influenza virus inactivating performance of the filter 16 impregnated with a tea extract drops proportionally as dust is trapped and accumulated in the antiviral filter 14. As moisture is sprayed to the filter 16 from bottom of the antiviral filter 14, this moisture transfers to the entirety of the trapped dust particles. The tea extract has the nature that it is easily dissolved in water.

The influenza viruses attached to the moistened dust particles become more liable to contact with the tea extract eluted from the filter 16, resulting in an elevated influenza virus inactivating performance of the filter and an improvement of its durability.

The water unnecessary for moistening is returned to the water tank 33, and only a necessary mount of moisture is supplied efficiently into the room.

As described above, the gargling cup according to the present invention comprises a cup having a gargling agent deposited or coated thereon so that by merely pouring water into the cup, there is instantly formed a liquid for gargling in the cup, allowing a person to perform gargling effective for preventing cold.

Also, because of use of a tea polyphenol, which is a natural tea extract, as the gargling agent, the gargling agent is high in safety and also has a high inactivating action against the pathogenic viruses of cold such as influenza virus, so that a cup for gargling effective for preventing cold is provided.

Further, in accordance with the present invention, since an effective amount of the gargling agent for preventing cold can be impregnated, coated or incorporated in or on the cup body, it is possible to obtain a garglewash with an effective concentration of gargling agent by merely pouring water into the cup.

Moreover, by making the cup structure foldable, there is provided a lightweight and compact cup which is convenient to carry. You can carry with you a plurality of gargling cups as a compact aggregate so that you can perform effective gargling whenever and where ever he or she wants as many times as the number of the cups even when you are away from home.

Moreover, according to the antiviral mask of the present invention, the viruses trapped by a nonwoven fabric impregnated with a tea extract can be inactivated by the action of said tea extract so that it is possible to prevent the captured infectious viruses from being rescattered or entering the mask wearer's lung with breathing.

Incorporation of an electret filter provides an antiviral mask with further improved virus trapping performance.

Further, by laminating a white nonwoven fabric on the front side, there can be obtained an antiviral mask which is elevated in virus trapping performance and elongated in service life due to the increase of nonwoven fabric and can definitely indicate the time for change of the filter by discoloration of the white nonwoven fabric.

Still further, by specifying the tea extract used, it is possible to provide an antiviral mask in which the impurities of the tea extract are reduced and which can be easily produced commercially and is enhanced in virus inactivating performance.

Incorporation of a deodorizing filter can provide an antiviral mask which can eliminate the odor from the mask and the smell of the air to be taken in and is capable of deodorizing foul breath.

According to the antiviral filter, air cleaner and air cleaner-humidifier of the present invention, by combining a dust collecting filter and a filter impregnated with a tea extract, it is possible to inactivate the viruses trapped by the filter, to prevent rescatter of the trapped active viruses and to enhance the virus trapping performance.

According to the antifungal, antibacterial and antiviral filter of the present invention, convenient effects may be obtained in that the pollution of fungi, bacteria and viruses may be decreased.

By using the tea extract which is gentle to a human body, the effect in that the filter may be easily prepared is obtained.

The use of a substance which is contained in the tea extract may improve the abilities of activating and inactivating bacteria and viruses, and high processability may be obtained.

The killing performance to fungi may be improved by using the antifungal agent having a low reactivity with the antibacterial and antiviral agents. There is merit in that the industrial production is possible.

By laminating the nonwoven fabric having the antifungal agent applied with the nonwoven fabric having the antibacterial and antiviral agents applied, fungi, bacteria and viruses may be effectively trapped, killed and inactivated and the effect for preventing from their growth on the filter may be obtained.

By mixing the antifungal agent with the antibacterial and antifungal agent and applying the mixture to the nonwoven fabric, the processability thereof may be improved and the time for producing the filter may be shortened.

By imparting the deliquescency to the antifungal, antibacterial and antiviral filter, the agents may be penetrated in the microorganisms and the growth thereof on the surface of the filter may be prevented.

By applying the antibacterial and antiviral agents to the nonwoven fabric having the antifungal agent applied, the trapping ability of the nonwoven fabric may be increased and the cost for producing the filter may be decreased.

By incorporating a preliminary charging means, it is possible to provide an air cleaner with further improved virus trapping performance.

Also, by incorporating an electroconductive nonwoven fabric, an air cleaner is provided which is enhanced in virus trapping performance of the antiviral filters including the filter impregnated with a tea extract and further prolonged in service life to elongate the time limit for change of the filter for new one.

Further, by specifying the minimum concentration of the tea extract necessary for inactivating the influenza viruses, it is possible to provide an antiviral filter and an air cleaner which are reduced in production cost and facilitated in quality management.

Also, by drying the tea extract impregnated in the antiviral filter, it is possible to oxidize the tea extract and reduce its odor density to eliminate the unpleasant feeling of the air released from the air outlet.

Further, by giving moisture to the air passed through the filter in an air cleaner-humidifier, it is possible to expedite inactivation of the viruses by the filter impregnated with a tea extract.

What is claimed is:

1. An air cleaner comprising a laminate of a dust collecting filter disposed on the upstream side, a tea extract of a polyphenol, and a filter impregnated with said tea extract.

2. An air cleaner according to claim 1, wherein said laminate comprises said dust collecting filter disposed on the upstream side, said tea extract of a polyphenol, and said filter impregnated with said tea extract being impregnated with said tea extract in a concentration of 0.5 g/m² or more.

3. An air cleaner comprising a laminate of a dust collecting filter disposed on the upstream side, a tea extract of a polyphenol, and a filter in which said tea extract has been impregnated and dried.

4. An air cleaner according to claim 3, wherein said laminate comprises said dust collecting filter disposed on the upstream side, a tea extract of a polyphenol, and said filter impregnated with said tea extract has been impregnated with said tea extract in a concentration of 0.5 g/m² or more and dried.

5. An air cleaner according to claim 2, wherein said laminate comprises said dust collecting filter disposed on the upstream side, a tea extract of a polyphenol, and said filter impregnated with said tea extract has been impregnated with said tea extract in the concentration of 0.5 g/m² or more, and further comprising a preliminary electric charging means upstream of said dust collecting filter.

6. An air cleaner according to claim 2, wherein said laminate comprises said dust collecting filter disposed on the upstream side, a tea extract of a polyphenol, and a filter impregnated with said tea extract in the concentration of 0.5 g/m² or more, and an electroconductive nonwoven fabric disposed downstream of said laminate.

7. An air cleaner according to claim 5, wherein said filter in which said tea extract has been impregnated is a filter in which said tea extract has been impregnated in the concentration of 0.5 g/m² or more and dried.

8. An air cleaner according to claim 6, wherein said filter in which said tea extract has been impregnated is a filter in which said tea extract has been impregnated in the concentration of 0.5 g/m² or more and dried.

9. An air cleaner according to claim 1, 2, 3, 4, 5, 6, 7, or 8, wherein the tea polyphenol is at least one virus inactivating agent selected from epigallocatechin gallate, epicatechin gallate, epigallocatechin, epicatechin, (+) catechin, their isomers, free theaflavine, theaflavine monogallate A, theaflavine monogallate B and theaflavine digallate.

10. An air cleaner according to claim 1, 2, 3, 4, 5, 6, 7 or 8, wherein said laminate comprises an antifungal, antibacterial and antiviral filter.

11. An air cleaner-humidifier comprising the air cleaner according to claim 1, 2, 3, 4, 5, 6, 7 or 8, and a means for flowing down water from top of the filter impregnated with said tea extract.

12. An air cleaner-humidifier comprising the air cleaner according to claim 1, 2, 3, 4, 5, 6, 7 or 8, and an ultrasonic vibratory membrane for spraying water upward from bottom of the filter impregnated with said tea extract.

13. An air cleaner according to claim 1 or 3, wherein said tea polyphenol, which is said tea extract, is present in sufficient concentration to be a virus inactivating agent.

14. An air cleaner according to claim 10, wherein the tea polyphenol is at least one virus inactivating agent selected from epigallocatechin gallate, epicatechin gallate, epigallocatechin, epicatechin, (+) catechin, their isomers, free theaflavine, theaflavine monogallate A, theaflavine monogallate B and theaflavine digallate.

15. An air cleaner-humidifier according to claim 11, wherein the tea polyphenol is at least one virus inactivating agent selected from epigallocatechin gallate, epicatechin gallate, epigallocatechin, epicatechin, (+) catechin, their isomers, free theaflavine, theaflavine monogallate A, theaflavine monogallate B and theaflavine digallate.

16. An air cleaner-humidifier according to claim 12, wherein the tea polyphenol is at least one virus inactivating agent selected from epigallocatechin gallate, epicatechin gallate, epigallocatechin, epicatechin, (+) catechin, their isomers, free theaflavine, theaflavine monogallate A, theaflavine monogallate B and theaflavine digallate.

17. An air cleaner comprising an antifungal, antibacterial and antiviral filter comprising a dust-collecting filter comprising non-woven fabric to which is applied an antifungal material, an antibacterial material and an antiviral material.

18. An air cleaner according to claim 17, wherein the antibacterial and antiviral material is a tea extract of a polyphenol.

19. An air cleaner according to claim 17, wherein the tea polyphenol used as the virus inactivating agent is at least one substance selected from epigallocatechin gallate, epicatechin gallate, epigallocatechin, epicatechin, (+) catechin, their isomers, free theaflavine, theaflavine monogallate A, theaflavine monogallate B and theaflavine digallate.

20. An air cleaner according to claim 17, wherein the antifungal material is dispersable with the antibacterial and antiviral agent.

21. An air cleaner according to claim 17, wherein the filter comprises a layered filter of non-woven fabric to which the antifungal material, the antibacterial material and the antiviral material has been applied.

22. An air cleaner according to claim 17, wherein the filter comprises a laminate comprising a layer of non-woven fabric to which antifungal material has been applied and a layer of non-woven fabric to which antibacterial and antiviral material has been applied.

23. An air cleaner according to claim 17, wherein a mixture of the antifungal material, the antibacterial material and the antiviral material has been applied to the filter.

24. An air cleaner according to claim 17, wherein a surfactant is blended in an antifungal agent to form the antifungal material to have a delinquency.

25. An air cleaner according to claim 17, made by a process comprising applying the antifungal material to the dust collecting filter, and then applying a tea extract which is the antibacterial and antiviral material to the dust collecting filter.

* * * * *